(12) United States Patent
Kulichikhin et al.

(10) Patent No.: US 7,217,853 B2
(45) Date of Patent: May 15, 2007

(54) COMPOSITION FOR CUSHIONS, WOUND DRESSINGS AND OTHER SKIN-CONTACTING PRODUCTS

(75) Inventors: Valery G. Kulichikhin, Moscow (RU); Shoreh Parandoosh, Menlo Park, CA (US); Mikhail M. Feldstein, Moscow (RU); Sergey Antonov, Moscow (RU); Gary W. Cleary, Los Altos Hills, CA (US)

(73) Assignee: Corium International, Inc., Redwood City, CA (US)

( * ) Notice: Subject to any disclaimer, the term of this patent is extended or adjusted under 35 U.S.C. 154(b) by 223 days.

(21) Appl. No.: 10/227,623

(22) Filed: Aug. 21, 2002

(65) Prior Publication Data

US 2003/0225356 A1 Dec. 4, 2003

Related U.S. Application Data

(60) Provisional application No. 60/383,504, filed on May 24, 2002.

(51) Int. Cl.
*A61F 13/00* (2006.01)

(52) U.S. Cl. .............. 602/41; 128/889; 106/205.01

(58) Field of Classification Search ............ 602/41–53; 128/888, 889; 424/443–444; 106/205.01, 106/123.11
See application file for complete search history.

(56) References Cited

U.S. PATENT DOCUMENTS

| | | | |
|---|---|---|---|
| 4,093,673 A | 6/1978 | Chang et al. | |
| 4,231,369 A | 11/1980 | Sorensen et al. | |
| 4,867,748 A | 9/1989 | Samuelsen | |
| 5,300,291 A | 4/1994 | Sablotsky et al. | |
| 5,344,394 A * | 9/1994 | Gyory et al. | ............. 604/20 |
| 5,492,943 A | 2/1996 | Stempel | |
| 5,527,271 A | 6/1996 | Shah et al. | |
| 5,643,187 A | 7/1997 | Næstoft et al. | |
| 5,656,286 A | 8/1997 | Miranda et al. | |
| 5,719,197 A | 2/1998 | Kanios et al. | |
| 5,830,932 A | 11/1998 | Kay | |
| 5,948,433 A | 9/1999 | Burton et al. | |
| 6,201,164 B1 | 3/2001 | Wulff et al. | |
| 6,316,022 B1 | 11/2001 | Mantelle et al. | |
| 2003/0100654 A1 * | 5/2003 | Chheang et al. | ............ 524/445 |

FOREIGN PATENT DOCUMENTS

WO WO 99/54422 10/1999

* cited by examiner

*Primary Examiner*—Henry Bennett
(74) *Attorney, Agent, or Firm*—Mintz, Levin, Cohn, Ferris, Glovsky and Popeo, P.C.

(57) ABSTRACT

A skin-contacting adhesive composition is described which has improved initial tack, long-term adhesion, water uptake and translucency characteristics and may be prepared by melt extrusion. Uses of these compositions are also described, for example, their use in wound dressings.

54 Claims, 2 Drawing Sheets

COMPOSITION FOR CUSHIONS, WOUND DRESSINGS AND OTHER SKIN-CONTACTING PRODUCTS

CROSS REFERENCE TO RELATED APPLICATIONS

This application claims priority under 35 U.S.C. § 119(e)(1) to U.S. Provisional Application Ser. No. 60/383,504 filed May 24, 2002.

FIELD OF THE INVENTION

This invention relates generally to skin-contacting adhesive compositions, and more particularly relates to a novel composition useful in a variety of contexts including as a wound dressing, cushion, or the like that is applied to an individual's skin or other body surface. The assignees of this application, Corium International, Inc. and the A.V. Topchiev Institute of Petrochemical Synthesis, Russian Academy of Sciences, are parties to a joint research agreement covering work in this and other fields.

BACKGROUND OF THE INVENTION

Various types of bandages and wound dressings are known and used to protect wounds and burns. Typically, wound dressings are fabricated with an absorbent material so that wound exudate is removed and the wound dries, facilitating healing. Wound dressings may also contain one or more pharmacologically active agents such as antibiotics, local anesthetics, or the like. Commonly used wound dressings include fibrous materials such as gauze and cotton pads, which are advantageous in that they are absorbent but problematic in that fibers may adhere to the wound or newly forming tissue, causing wound injury upon removal. Other wound dressings have been prepared with foams and sponges, but the absorbance of these materials is often limited. Furthermore, such wound dressings require the use of adhesive tape, as they are not themselves adhesive. Finally, many of these wound dressings are not translucent or transparent, thus rendering it difficult to monitor healing without removal of the dressing.

To improve the absorbance of conventional fibrous wound dressings, water-swellable polymers or "hydrogels" have been incorporated into gauze or other fibrous materials for application to a wound. For example, U.S. Pat. No. 5,527,271 to Shah, et al. describes a composite material made from a fibrous material, such as cotton gauze, impregnated with a thermoplastic hydrogel-forming copolymer containing both hydrophilic and hydrophobic segments. While the wound dressings are described as having increased absorptive capacity, the adhesion of fibers to the wound or newly forming tissue remains a significant disadvantage.

Another approach has been to use water-swellable polymeric materials instead of gauze, cotton, and the like. Wound-contacting surfaces made of such materials are not only more absorbent than conventional fibrous materials, they are also advantageous in that there is no risk of fiber adhesion during wound healing and upon removal of the wound dressing. Such wound dressings are disclosed, for example, in U.S. Pat. No. 4,867,748 to Samuelsen, which describes the use of an absorbent wound-contacting composition made from a water-soluble or water-swellable hydrocolloid blended with or dispersed in a water-insoluble, viscous, elastomeric binder. U.S. Pat. No. 4,231,369 to Sørensen et al. describes "hydrocolloid plasters" as sealing materials for ostomy devices, the materials consisting of a continuous hydrophobic phase made from a hydrophobic pressure-sensitive adhesive, an elastomeric plasticizer, and a tackifying resin, with a discontinuous phase dispersed therein consisting of a water-soluble or water-swellable polymer. Such plasters are also described in U.S. Pat. No. 5,643,187 to Naestoft et al. U.S. Pat. No. 6,201,164 to Wulff et al. describes a somewhat different type of hydrocolloid wound gel, consisting of a water-insoluble, water-swellable, crosslinked cellulose derivative, an alginate, and water.

Hydrogel bandages have also been employed in wound dressings, as described, for example, in U.S. Pat. No. 4,093,673 to Chang et al. Hydrogel bandages are made from a liquid absorbing crosslinked polymer and have a high water content prior to use. The high water content causes the hydrogel to exhibit very little or no adhesion, requiring the use of adhesive tape or a plaster such as $2^{nd}$ Skin® dressing available from Spenco Medical Ltd., U.K.

However, in spite of the advances in the art, numerous problems continue to be encountered with gel-based wound dressings made with hydrocolloids and hydrogels. The reason for this is, in part, that there are conflicting requirements for an ideal material. The material should not be so adhesive that it tends to adhere to a wound and thus cause pain or further injury upon removal. However a wound dressing should adhere sufficiently to a body surface so that separate adhesive tapes and adhesive plasters are not necessary. Peripheral adhesives can be used, but require an additional manufacturing step. In addition, a wound dressing should conform to the contours of the skin or other body surface, both during motion and at rest. For wound dressings that also serve as a cushioning pad, higher cohesive strength materials should be used, without any loss in adhesion.

Many of these problems can be solved by using a skin-contacting adhesive that also serves as a bandage or wound dressing. The ideal skin-contacting adhesive would display very high swelling upon contact with water, exhibit little or no cold flow during use, and could be easily tailored during manufacture to optimize properties such as adhesive strength, cohesive strength, and hydrophilicity. It would also be desirable to be able to manufacture a skin-contacting adhesive using a simple extrusion process, obviating the need for organic solvents and the conventional, time-consuming blending and casting method.

Another desired goal, with respect to wound dressings, would enable a skin-contacting adhesive to be prepared that meets all of the foregoing criteria and is, in addition, translucent. With a translucent material, it becomes possible to view the degree of wound healing through the dressing, in turn meaning that the dressing does not need to be removed, changed, or partially peeled back from the skin in order to assess the degree of healing.

It would also be ideal if a skin-contacting adhesive met all of the above criteria and could also be adapted for uses other than wound healing. Such uses might include, by way of example, fabrication of transdermal drug delivery devices, preparation of medicated gels for topical and transdermal pharmaceutical formulations, use in pressure-relieving cushions (which may or may not be medicated), use as sealants for ostomy devices and prostheses, use as conductive adhesives for attachment of electroconductive articles such as electrodes to the skin, and the like.

The present invention addresses those needs by providing a skin-contacting adhesive that meets all of the aforementioned criteria.

SUMMARY OF THE INVENTION

One aspect of the invention relates to a skin-contacting adhesive (SCA) composition comprised of a hydrophobic phase and a hydrophilic phase, where the hydrophobic phase comprises a hydrophobic polymer, at least one elastomeric plasticizer and a tackifying resin; and the hydrophilic phase comprises at least one material selected from the group consisting of low molecular weight cellulose derived polymers and naturally occurring polysaccharides, at least one high molecular weight cellulose derived polymer, and reinforcing clay particles.

Another aspect of the invention pertains to a skin-contacting adhesive composition comprised of a hydrophobic phase and a hydrophilic phase, where the hydrophobic phase comprises: a hydrophobic polymer selected from the group consisting of polyisobutylene, butyl rubbers, natural rubber adhesives, vinyl ether polymers, polysiloxanes, polyisoprene, styrene-isoprene-styrene block copolymers, styrene-butadiene-styrene block copolymers, isobutylene-isoprene copolymers, butadiene acrylonitrile rubber, polychloroprene, ethylene-propylene-diene terpolymers, and combinations thereof; at least one elastomeric plasticizer and a tackifying resin; and the hydrophilic phase comprises: at least one material selected from the group consisting of low molecular weight cellulose derived polymers and naturally occurring polysaccharides, at least one high molecular weight cellulose derived polymer and reinforcing clay particles.

Still another aspect of the invention pertains to an adhesive cushion for application to the skin, comprising a skin-contacting layer of an adhesive composition comprised of a hydrophobic phase and a hydrophilic phase, where the hydrophobic phase comprises a hydrophobic polymer, at least one elastomeric plasticizer and a tackifying resin; and the hydrophilic phase comprises at least one material selected from the group consisting of low molecular weight cellulose derived polymers and naturally occurring polysaccharides, at least one high molecular weight cellulose derived polymer and reinforcing clay particles; and laminated thereto, a backing layer.

Yet another aspect of the invention relates to a wound dressing comprising a laminated composite of a body facing layer having a body-contacting surface, and an outwardly facing non-occlusive backing layer, wherein at least a portion of the body-contacting surface is comprised of a skin-contacting adhesive comprised of a hydrophobic phase and a hydrophilic phase, where the hydrophobic phase comprises a hydrophobic polymer, at least one elastomeric plasticizer and a tackifying resin; and the hydrophilic phase comprises at least one material selected from the group consisting of low molecular weight cellulose derived polymers and naturally occurring polysaccharides, at least one high molecular weight cellulose derived polymer and reinforcing clay particles.

Another aspect of the invention relates to a transdermal drug delivery device comprised of a drug reservoir containing a therapeutically effective amount of an active agent, an outwardly facing backing layer, and a means for affixing the device to a body surface comprising a skin-contacting adhesive composition, where the adhesive composition comprises a hydrophobic phase comprising a hydrophobic polymer, at least one elastomeric plasticizer and a tackifying resin; and a hydrophilic phase comprising at least one material selected from the group consisting of low molecular weight cellulose derived polymers and naturally occurring polysaccharides, at least one high molecular weight cellulose derived polymer and reinforcing clay particles.

Still another aspect of the invention relates to a transdermal drug delivery device comprised of a drug reservoir containing a therapeutically effective amount of an active agent and an outwardly facing backing layer, wherein the drug reservoir is comprised of a skin-contacting adhesive composition, wherein the adhesive composition comprises a hydrophobic phase comprising a hydrophobic polymer, at least one elastomeric plasticizer and a tackifying resin; and a hydrophilic phase comprising at least one material selected from the group consisting of low molecular weight cellulose derived polymers and naturally occurring polysaccharides, at least one high molecular weight cellulose derived polymer and reinforcing clay particles.

Yet another aspect of the invention relates to a skin-contacting adhesive composition comprised of a hydrophobic phase and a hydrophilic phase, wherein the hydrophilic phase has a fiber-particle morphology. The hydrophilic phase is made of: fibers of a liquid crystalline high molecular weight cellulose derived polymer; ordered particles of clay; and randomly distributed spherical solid droplets of a low molecular weight cellulose derived polymer, naturally occurring polysaccharide, or combination thereof.

DETAILED DESCRIPTION OF THE INVENTION

Figure 1:
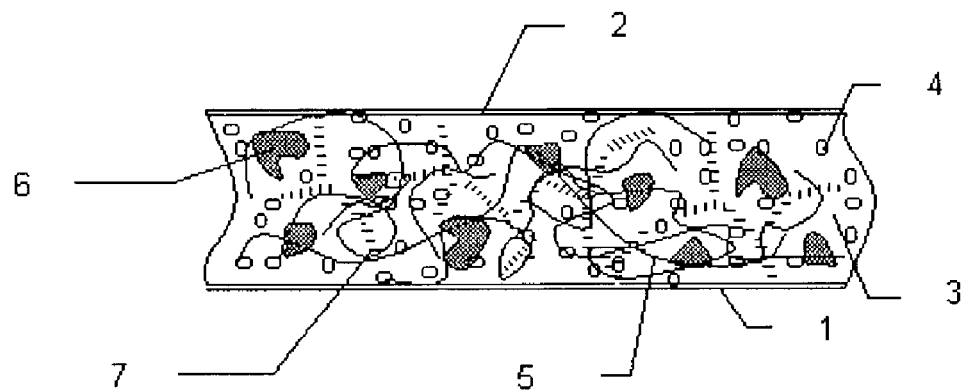
FIG. 1 illustrates the morphology of the skin-contacting adhesive of the invention.

The present invention is a skin-contacting adhesive that finds utility in numerous applications. In particular, due to the skin-contacting adhesive (SCA) properties under moist and load-bearing conditions, it finds particular utility for medical films used in foot care. For example, the adhesive can be applied to the sole of the foot, to the toes or to any other location on the foot to treat pain caused by a callus, corn, bunion, or blister, by providing a cushion effect. The skin-contacting adhesive composition is comprised of a hydrophobic phase and a hydrophilic phase. The hydrophobic phase includes a hydrophobic polymer, at least one elastomeric plasticizer and a tackifying resin. The hydrophilic phase includes at least one low molecular weight cellulose derived polymer or naturally occurring polysaccharide, or a combination thereof. The hydrophilic phase also includes at least one high molecular weight cellulose derived polymer and reinforcing clay particles.

The skin-contacting adhesive of the invention provides for prolonged hydrations such that it is able to absorb water found in the environment or from the body surface to which it is applied. In particular, it is preferred that the adhesive remain translucent upon water uptake over a typical wearing time of 72 hours. The skin-contacting adhesive has rapid initial tack in that it grabs quickly to the skin surface during application, is pressure and body sensitive and able to maintain excellent adhesion while subjected to load bearing forces, such as those experienced when the adhesive is positioned on a lower foot surface. In addition, the skin-contacting adhesive is preferably skin and user friendly for at least 72 hours of continuous wear.

The hydrophilic phase of the skin-contacting adhesive of the invention also has a unique fiber-particle morphology, where the high molecular weight cellulose derived polymer (as a liquid crystal) is present as fibers, the clay component is present as ordered particles, and the low molecular weight cellulose derived polymer and/or naturally occurring polysaccharide is present as randomly distributed spherical solid droplets.

The aforementioned characteristics are readily achieved by careful selection of the individual components in the adhesive composition, as well as adjusting one or more parameters during fabrication.

Before describing the detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive and it is further to be understood that unless otherwise indicated this invention is not limited to specific materials, active agents, additives, and so forth, as such may vary. For example, when an example is said to "include" a specific feature, that is intended to imply that it may have that feature but not that such examples are limited to those that include that feature. Thus, for example, reference to "a cellulose derived polymer" includes a mixture of two or more such polymers, and so forth. Finally, it must be noted that, as used in this specification and the appended claims, the singular forms "a," "an" and "the" include plural referents unless the context clearly dictates otherwise. Thus, for example, reference to "an active agent" includes a mixture of two or more such agents, and the like.

I. DEFINITIONS

In describing and claiming the present invention, the following terminology will be used in accordance with the definitions set out below.

The terms "hydrophobic polymer" and "hydrophilic polymer" are intended to be defined relative to the amount of water vapor absorbed by polymers at 100% relative humidity. According to this classification, hydrophobic polymers absorb only up to 1 wt % of water at 100% relative humidity (rh), while moderately hydrophilic polymers absorb 1–10 wt % of water, hydrophilic polymers are capable of absorbing more than 10 wt % of water, and hygroscopic polymers absorb more than 20 wt % of water.

The terms "tack" and "tacky" are qualitative. However, the terms "substantially nontacky", "slightly tacky" and "tacky," as used herein, may be quantified using the values obtained by a PSA Tack Determination/Polyken Probe method (Solutia, Inc.). By "substantially nontacky" is meant an adhesive that has a tack value that is less than about 25 g-cm/sec, by "slightly tacky" is meant an adhesive that has a tack value in the range of about 25 g-cm/sec to about 100 g-cm/sec, and by "tack" is meant an adhesive that has a tack value of at least 100 g-cm/sec.

The term "translucent" is used to signify a material capable of transmitting light so that objects or images can be seen through the material. Translucent materials herein may or may not be "transparent," meaning that the material is optically clear. The term "translucent" indicates that a material is not "opaque," in which case objects and images either cannot be seen through the material.

The term "active agent" refers to a chemical material or compound suitable for topical or transdermal administration and that induces a desired effect. The terms include agents that are therapeutically effective, prophylactically effective, and cosmetically effective agents. Also included are pharmaceutically acceptable, pharmacologically active derivatives of those active agents specifically mentioned herein, including, but not limited to, salts, esters, amides, prodrugs, active metabolites, inclusion complexes, analogs, and the like, which also induce the desired effect. The terms "active agent", "drug" and "therapeutic agent" are used interchangeably herein.

By "transdermal" delivery is meant administration of an active agent to the skin surface of an individual so that the agent passes through the skin tissue and into the individual's blood stream. The term "transdermal" is intended to include transmucosal administration, i.e., administration of a drug to the mucosal (e.g., sublingual, buccal, vaginal, rectal) surface of an individual so that the agent passes through the mucosal tissue and into the individual's blood stream.

The term "body surface" is used to refer to skin or mucosal tissue, including the interior surface of body cavities that have a mucosal lining. The term "skin" should be interpreted as including "mucosal tissue" and vice versa.

The term "therapeutically effective amount" is intended to mean the amount of an active agent that is nontoxic but sufficient to provide the desired effect. The amount that is "effective" will vary from subject to subject, depending on the age and general condition of the individual, the particular active agent or agents, and the like. Thus, it is not always possible to specify an exact effective amount. However, an appropriate effective amount in any individual case may be determined by one of ordinary skill in the art using routine experimentation. Furthermore, the exact effective amount of an active agent incorporated into the adhesive of the invention is not critical, so long as the concentration is within a range sufficient to permit ready application of the formulation so as to deliver an amount of the active agent that is within a therapeutically effective range.

II. COMPOSITIONS

The desirable adhesive characteristics are achieved by selection of the individual components as well as adjusting one or more parameters during fabrication. For example, the adhesive strength of the adhesive can be controlled during manufacture in order to increase, decrease, or eliminate adhesion. This can be accomplished by varying the type and/or amount of different adhesive components, or by changing the mode of fabrication. For example, incorporating greater amounts of the elastomeric plasticizer and the tackifying resin in the hydrophobic phase will increase tack, while reducing the amounts of those components or incorporating detackifier additives or increasing the level of powdered hydrophilic components, will decrease tack. Also, with respect to the fabrication process, adhesives prepared using a conventional melt extrusion process tend to be more tacky, while adhesives prepared by a molding procedure tend to have lower tack. In addition, adhesives may be rendered translucent by changing the relative quantities of the components in the hydrophilic phase (e.g., by decreasing the amount of clay, the cellulose derived polymer or natural polysaccharides), or by changing the conditions (temperature, extrusion rate, thickness, etc.) of fabrication method.

Furthermore, the degree to which the adhesive will swell upon contact with water can be varied by selecting different water-swellable and water-soluble hydrophilic polymers and their ratio. Combination of water-swellable and water-soluble hydrophilic polymers allows us to control the swelling degree of SCA and to create a capability of SCA for re-application after their additional wetting.

The skin-contacting adhesive composition of the invention is comprised of a hydrophobic phase and a hydrophilic phase. Typically, the composition will be about 50–80 wt % hydrophobic phase and about 20–50 wt % hydrophilic phase. One preferred embodiment has about 60–70 wt % hydrophobic phase and about 30–40 wt % hydrophilic phase.

The hydrophobic phase comprises a hydrophobic polymer, at least one elastomeric plasticizer and a tackifying resin, while the hydrophilic phase comprises at least one material selected from the group consisting of low molecular weight cellulose derived polymers and naturally occurring polysaccharides, at least one high molecular weight cellulose derived polymer and reinforcing clay particles. A typical composition is described below.

| Ingredient | Preferred Wt % range | More Preferred Wt % range |
|---|---|---|
| Hydrophobic polymers | 10–50 | 15–46 |
| Elastomeric plasticizers | 5–40 | 5–31 |
| Tackifying resin | 0.5–40 | 1–35 |
| High MW cellulose derived polymers | 5–40 | 5–32 |
| Low MW cellulose derived polymers (when present) | 1–20 | 3–17 |
| Naturally occurring polysaccharides (when present) | 2–40 | 5–20 |
| Clay particles | 2–30 | 3–20 |
| Optional ingredients | 0–20 | 0.1–10 |

As noted in the table, when a low MW cellulose derived polymer is included, the naturally occurring polysaccharide can be omitted and vice versa. Thus the invention includes compositions having only a low MW cellulose derived polymer, having only a naturally occurring polysaccharide or having both.

For those embodiments of the invention, where the hydrophilic phase comprises only low and high molecular weight cellulose derived polymers, i.e., no naturally occurring polysaccharides, a typical composition is described below.

| Ingredient | Preferred Wt % range | More Preferred Wt % range |
|---|---|---|
| High and Low MW Cellulose derived polymers | 12–60 | 18–45 |
| Clay particles | 2–10 | 3–6 |

Higher amounts of clay can be included in those embodiments where the hydrophilic phase includes at least one naturally occurring polysaccharide, alone or in combination with one or more low molecular weight cellulose derived polymers. A typical composition is described below.

| Ingredient | Preferred Wt % range | More Preferred Wt % range |
|---|---|---|
| Naturally occurring polysaccharides | 2–40 | 5–30 |
| Clay particles | 2–30 | 4–20 |

Exemplary composition are set forth below and in the Examples. The skin-contacting adhesive (SCA) finds utility in wound dressings, for example. The formulation of Cushions 1 and 2 lend themselves to cushions that will be load-bearing, for example to treat a callus under the foot, while the formulation of Cushion 3 is more suited to treat corns, blisters and bunions that are present on the top or sides of the foot.

| Ingredient | Weight Percent | | | |
|---|---|---|---|---|
| | SCA | Cushion 1 | Cushion 2 | Cushion 3 |
| Hydrophobic polymer | 19.0 | 20.0 | 20.0 | 20.0 |
| Elastomeric plasticizer | 14.5 | 15.0 | 15.0 | 19.0 |
| Tackifying resin | 28.0 | 25.5 | 25.5 | 25.5 |
| High MW cellulose derived polymer | 22.0 | 15.0 | 10.0 | 10.0 |
| Low MW cellulose derived polymer | 12.0 | — | 3.0 | 8.5 |
| Naturally occurring polysaccharide | — | 15.0 | 17.0 | 10.0 |
| Clay particles | 3.0 | 8.0 | 8.0 | 4.0 |
| Optional ingredients | 1.5 | 1.5 | 1.5 | 3.0 |

In the aforementioned skin-contacting adhesive and cushion formulations, an exemplary formulation utilizes a styrene-isoprene-styrene block copolymer, alone or in combination with a styrene-isoprene block copolymer, as the hydrophobic polymer; a low molecular weight polyisoprene rubber as the elastomeric plasticizer; a non-polar tackifying resin as the tackifying resin; hydroxypropylcellulose as the high and low MW cellulose derived polymers; and agar as the naturally occurring polysaccharide. Other materials that are also well suited for use in the invention, are described in detail below. In addition, a preferred embodiment includes a polyisobutylene adhesive material as the optional ingredient.

These percentages are intended to merely be illustrative of the compositions of the invention. There are other factors that can be taken into consideration when ascertaining the actual materials and quantities to be used in the formulations. For example, the weight ratios of certain materials can be selected so as to optimize the adhesive strength, cohesive strength and water sorbtion of the composition. These include the weight ratio of the hydrophobic phase and the hydrophilic phase; the weight ratio of the high MW cellulose derived polymers, low MW cellulose derived polymers or naturally occurring polysaccharides, and the reinforcing clay particles; and the weight ratio of the hydrophobic polymer, elastomeric plasticizer and tackifying resin.

Similarly, the weight ratios of these same materials can be selected so as to render the composition translucent, which is a desirable characteristic for some applications of the adhesive. Interestingly, the hydrophilic phase maintains its translucent characteristics in spite of its heterogeneous characteristic, i.e., the high molecular weigh cellulose derived polymers, as well as low MW cellulose derived polymers (when included) are in a melt phase and the clay particles, as well as the naturally occurring polysaccharides (when included) are in the dispersed phase.

A sketch of morphology of the hydrophobic phase of the SCA of the invention is shown in FIG. 1. This is intended to be illustrative and not limiting. The exemplary SCA has a backing layer 1 and a removable release liner 2. The hydrophobic phase 3 has a high molecular weight cellulose derivative 5 as well as clay particles 7. The hydrophobic phase further comprises a low Mw cellulose derivative 4 and/or a naturally occurring polysaccharide 6.

A. Hydrophobic Phase-Hydrophobic Polymer

Suitable hydrophobic polymers include, by way of illustration and not limitation, polyisobutylenes, butyl rubbers, natural rubber adhesives, vinyl ether polymers, polysiloxanes, polyisoprenes, styrene-isoprene-styrene block copolymers, styrene-butadiene-styrene block copolymers, isobutylene-isoprene copolymers, butadiene acrylonitrile rubber, polychloroprenes, ethylene-propylene-diene terpolymers, and combinations thereof. Styrene-isoprene-styrene block copolymers, styrene-butadiene-styrene block copolymers and butyl rubbers are particularly well suited for use in the invention.

In one embodiment of the invention, the hydrophobic polymer is a triblock styrenic copolymer such as styrene-isoprene-styrene (SIS) or styrene-butadiene-styrene (SBS) and can further comprises the diblock copolymer, styrene-isoprene (SI) block copolymer. Such mixtures can contain up to 45 wt % of the SI diblock copolymer.

Commercially available styrene-based block copolymers such as the Vector series (available from Dexco Polymers) are particularly useful in the invention. These include the SIS Vector 4111 (18 wt % styrene/82 wt % isoprene) and 4411 (44 wt % styrene/56 wt % isoprene) as well as SIS/SI mixtures such as Vector 4113 (18 wt % SI diblock; overall 15 wt % styrene/85 wt % isoprene), Vector 4114 (42 wt % SI diblock; overall 15 wt % styrene/85 wt % isoprene), Vector 4213 (25 wt % SI diblock; overall 25 wt % styrene/75 wt % isoprene) and Vector 4215 (18 wt % SI diblock; overall 30 wt % styrene/70 wt % isoprene).

In another embodiment of the invention, the hydrophobic polymer is a polyisoprene or a butyl rubber. Commercially available polyisoprenes such as the high molecular weight polyisoprene rubber Natsyn® 2210 (Goodyear Tire and Rubber), and butyl rubbers such as the high molecular weight butyl rubber BR 065 (Exxon), are particularly useful in the invention.

Accordingly, in one embodiment of the invention, the skin-contacting adhesive composition comprises of a hydrophobic phase and a hydrophilic phase, where the hydrophobic phase comprises a hydrophobic polymer selected from the group consisting of polyisobutylene, butyl rubbers, natural rubber adhesives, vinyl ether polymers, polysiloxanes, polyisoprene, styrene-isoprene-styrene block copolymers, styrene-butadiene-styrene block copolymers, isobutylene-isoprene copolymers, butadiene acrylonitrile rubber, polychloroprene, ethylene-propylene-diene terpolymers, and combinations thereof. The hydrophobic phase also contains at least one elastomeric plasticizer and a tackifying resin, while the hydrophilic phase comprises the low molecular weight cellulose derived polymer or naturally occurring polysaccharide, the high molecular weight cellulose derived polymers and the reinforcing clay particles.

In the case of unsaturated rubbers a curing agent may be added to fix the SCA structure and to prevent cold flow. Since it is desirable to reach the specific rheological properties of SCA, namely diminished cold flow, i.e., substantially total elastic recovery, unsaturated hydrophobic components (butyl rubber, natural rubber, synthetic polyisoprene rubber, etc.) are preferably crosslinked. Polymers containing double bonds undergo a process of chemical crosslinking with formation of covalent bonds. The density of the resultant chemical network should not be too high, in order to preserve the desired tack. The number of crosslinks in the volume unit can be controlled by the nature and amount of crosslinkers, as well as by the temperature-time procedure followed. Phenolformaldehyde resins and alkylphenolformaldehyde resins are suitable crosslinkers for butyl rubber, while dicumyl peroxide can be used for polyisoprenes.

The most convenient method of monitoring the degree of crosslinking involves measurement of the change in melt viscosity over time. The resulting rheokinetic curve demonstrates the rate of crosslinking and the plateau region corresponds to the completion of the chemical interaction of double bonds of unsaturated hydrophobic polymers with the crosslinkers. This rheokinetic curve is shown, for example, in FIG. 3.

In the case of triblock-copolymers, e.g. SIS or SBS, their solidification occurs as they cool due to the segregation of styrene blocks and their transition to glassy state. At ambient temperature the elastic recoil of triblock-copolymers formulations, exceeds 90%. The presence of elastomeric isoprene or butadiene blocks in the macromolecules of SIS and SBS, as well as the additional components of the hydrophobic phase (e.g., plasticizers), results in the desired tack and adhesive properties.

B. Hydrophobic Phase-Elastomeric Plasticizer

The elastomeric plasticizer is preferably selected so as to be compatible with triblock-copolymers, i.e., forms a solution with multiblock-copolymers inside the definite temperature-concentration region of the phase diagram. Thus, one of skill in the art can readily use phase diagrams of the hydrophobic phase components for guidance concerning the appropriate amounts of each component to use.

Suitable elastomeric plasticizers include block polymers having a "multiarmed $(AB)_x$" configuration, where for example, A is a polymerized block comprising aryl-substituted vinyl monomers, preferably styrene, α-methyl styrene, vinyl toluene, and the like, B is an elastomeric, conjugated polybutadiene or polyisoprene block, and x has a value of 3 or more. Preferred plasticizers are styrene-based polymers, particularly styrene-butadiene block copolymers and styrene-isoprene block copolymers, and combinations thereof. Many of these are readily available commercially, such as the styrene-isoprene block copolymer sold under the name LVSI 101 (Kraton).

The elastomeric plasticizer can also be a low molecular weight polyisobutylene, or a low molecular weight polyisoprene rubber (MW=20,000–100,000) such as cis-1,4 polyisoprene (e.g., Isolene® 400 or Isolene 40 from Elementis Performance Polymers), optionally mixed with paraffin oil.

In one embodiment of the invention, the hydrophobic phase-elastomeric plasticizer includes both a block polymer (e.g., styrene) and a low molecular weight polyisoprene rubber (e.g. cis-1,4 polyisoprene).

C. Hydrophobic Phase-Tackifying Resin

The tackifying resin is a relatively low molecular weight resin (weight average molecular weight generally less than about 50,000) having a fairly high glass transition temperature. Its function is to increase the strength of adhesion bonds. Tackifying resins include, for example, rosin derivatives, terpene resins, and synthetic or naturally derived petroleum resins. Preferred tackifying resins herein are generally non-polar tackifying resins selected from the group consisting of hydrogenated hydrocarbon resins, hydrocarbon resins and synthetic polyterpene resins. The tackifying resin is preferably miscible with hydrophobic polymer/plasticizer composition to provide a ternary solution. Commercially available resins within these classes include Regalrez 1085 (hydrogenated hydrocarbon resin) and Regalite Resins such as Regalite 9100 (partially hydrogenated hydrocarbon resin, available from Hercules); Escorez 1304 and Escorez 1102 (hydrocarbon resins), and Escorez 5380 (cyclicaliphatic hydrocarbon resin) available from Exxon Chemical Company, Wingtack 95 and Wingtack 85 (synthetic polyterpene resins), available from Goodyear Tire and Rubber.

D. Hydrophilic Phase-Low and High MW Cellulose Derived Polymers

The cellulose derived polymers useful in the skin-contacting adhesive of the invention are preferably water-swellable or water-soluble hydrophilic polymers. The term "high" molecular weight (MW) refers to those cellulose derived polymers having a molecular weight within the range of about 300–1,150 kg/mole, more typically within the range of about 350–850 kg/mole. The term "low" molecular weight (MW) refers to those cellulose derived polymers having a molecular weight within the range of about 80–140 kg/mole.

Several water-soluble cellulose derivatives can be melted and introduced to the formulation by mixing through the melt state. This feature leads to possibility to control the morphology of hydrophilic part of SCA. Depending upon the molecular weight of the cellulose derived polymer, it can form either spherical droplets or long liquid jets at mixing, transforming to solid fibers upon cooling.

Suitable water-soluble cellulose derived polymers include hydroxypropylcellulose (HPC) of different MW. HPC melts at ~120–130° C. and forms long fibers upon agitation, which then penetrate the formulation. Since HPC melts are liquid-crystalline, i.e., the HPC chains are packed with a definite correlation of long axis, giving so-called nematic or cholesteric structure, the capability to change the shape of the droplets at deformation ("strain susceptibility") at mixing is higher than for isotropic polymer melts. For that reason, HPC polymers readily form long liquid threads that, upon cooling, provides for long solid fibers having excellent molecular orientation along the long axis of fibers. These fibers serve as channels for fast moistures transportation from the wound/skin to the depth of SCA.

Thus, the combination of HPC of different molecular weight provides for the creation of a droplet/fiber morphology of the hydrophilic phase of the SCA, which provides rapid moisture penetration and high water uptake during use.

The HPC-water phase diagram contains three different phase states at T<43° C., as the HPC content increases: up to 35% HPC, liquid-crystalline solution (up to 80% HPC, and crystalhydrate (additive compound of one mole of HPC and six moles of water). At T>43° C. the crystalhydrate decomposes to HPC and free water. The rate of polymer interaction with water can be expressed by the interdiffusion coefficient onto interface, $D_v$, determined by optical interference. Its values for different systems (including PVP as a reference) are presented below.

| Polymer | $D_v 10^{11}$, m²/c |
|---|---|
| PVP (MW = $10^6$) | 4.0 |
| Na—CMC (type 7 LF) | 2.0 |
| HPC (MW = 80,000) | 1.8 |
| HPC (MW = 140,000) | 1.7 |
| HPC (MW = 370,000) | 1.5 |
| HPC (MW = 850,000) | 1.3 |
| HPC (MW = 1,150,000) | 1.2 |

PVP interacts with water very quickly, but this leads to softening SCA as whole. HPC's and Na-CMC have comparable interdiffusion coefficients, but HPC is able to form a swelled (gel-like) layer, which can reduce (or control) the further penetration of water into the polymer. In addition, a combination of different grades of HPC allows for regulating the rate of moisture penetration. In a preferred embodiment, the weight ratio of low MW to high MW cellulose derived polymer is about 1:1 to 1:2.

Suitable cellulose derived polymers include, but are not limited to, hydratecellulose (cellophane), hydroxypropylcellulose (HPC), hydroxypropylmethylcellulose (HPMC), and sodium carboxymethylcellulose (Na-CMC).

There are numerous commercially available cellulose derived polymers that can be used in the adhesive of the invention. For example, EF (molecular weight of 80 kg/mole), LF (molecular weight of 80–95 kg/mole), JF (molecular weight of 140 kg/mole), GF (molecular weight of 370 kg/mole), MF (molecular weight of 850 kg/mole) and HF (molecular weight of 1,150 kg/mole) are various grades of HPC polymers available under the tradename Klucel® (Hercules Inc.).

E. Hydrophilic Phase-Naturally Occurring Polysaccharides

Naturally occurring polysaccharides include materials such as agars of various origin; alginates including alginic acid, salts of alginic acid (e.g., calcium alginate, potassium alginate, sodium alginate), and derivatives of alginic acid (e.g. propylene glycol alginate, Kelcoloid®, Monsanto); carrageenans including kappa-, iota- and lambda carrageenans; chitin; chitosan; glucomannan; gum guar (TIC Gums); gellan gum (Kelcogel®, Monsanto); locust bean gum; pectins such as pectin and amylopectin; pullulan; starches (e.g., potato starch acetate, Clearam® CH10, Roquette); xanthans such as xanthane gum; and combinations thereof.

Particularly preferred naturally occurring polysaccharides include, by way of illustration and not limitation, agar, gum guar, gellan gum, calcium alginate, starches, and so forth. The polysaccharide may be charged, and thus able to interact with the clay particles. Typically, the polysaccharides are water-swellable at room temperature with very high water uptake. Some may also dissolve in boiling water and form a gel at cooling. The polysaccharides provides for enhanced accumulation and storage of moisture in the SCA.

In a preferred embodiment, the weight ratio of naturally occurring polysaccharide to cellulose derived polymer is about 1:1 to 2:1.

F. Hydrophilic Phase-Reinforcing Clay Particles

The clay particles used in the skin-contacting adhesive of the invention are responsible for many of the beneficial aspects of the invention. For example, the clay particles: help to provide a wicking action to remove moisture from the skin surface and store it; reinforce the yield behavior that prevents the cold flow; help the composition maintain its adhesive nature as well as providing structural support to supply the high elastic recoil at application of SCA on the sole of foot, etc.

In general, clay materials are typically plastic when moist but hard when heated, and are often composed mainly of fine particles of hydrous aluminum silicates, alone or in combination with other minerals. In particular, suitable clay particle materials are selected from the group consisting of phyllosilicates (layered silicates) and layered double hydroxides (minerals and synthetic materials with positively charged brucite-type layers of mixed metal hydroxides). Such materials are described in detail in references such as "Polymer-Clay Nanocomposites", ed. T. J. Pinnavaia and G. W. Beall (Wiley Series in Polymer Science, John Wiley & Sons, Ltd., ©2000), the disclosure of which is incorporated herein by reference.

In one embodiment of the invention, the phyllosilicate is selected from the group consisting of allophane (hydrated aluminum silicate); apophyllite (hydrated potassium sodium calcium silicate hydroxide fluoride); bannisterite (hydrated potassium calcium manganese iron zinc aluminum silicate hydroxide); carletonite (hydrated potassium sodium calcium silicate carbonate hydroxide fluoride); cavansite (hydrated calcium vanadate silicate); chrysocolla (hydrated copper aluminum hydrogen silicate hydroxide); clay minerals (described in detail below); delhayelite (hydrated sodium potassium calcium aluminum silicate chloride fluoride sulfate); elpidite (hydrated sodium zirconium silicate); fedorite (hydrated potassium sodium calcium silicate hydroxide fluoride); franklinfumaceite (calcium iron aluminum manganese zinc silicate hydroxide); franklinphilite (hydrated potassium manganese aluminum silicate); gonyerite (manganese magnesium iron silicate hydroxide); gyrolite (hydrated calcium silicate hydroxide); kanemite; kenyaite; leucosphenite (hydrated barium sodium titanium boro-silicate); magadiite; makatite; micas such as biotite (potassium iron magnesium aluminum silicate hydroxide fluoride), lepidolite (potassium lithium aluminum silicate hydroxide fluoride), muscovite (potassium aluminum silicate hydroxide fluoride), paragonite (sodium aluminum silicate hydroxide), phlogopite (potassium magnesium aluminum silicate hydroxide fluoride) and zinnwaldite (potassium lithium aluminum silicate hydroxide fluoride); minehillite (hydrated potassium sodium calcium zinc aluminum silicate hydroxide); nordite (cerium lanthanum strontium calcium sodium manganese zinc magnesium silicate); octosilicate; pentagonite (hydrated calcium vanadate silicate); petalite (lithium aluminum silicate); prehnite (calcium aluminum silicate hydroxide); rhodesite (hydrated calcium sodium potassium silicate); sanbomite (barium silicate); serpentines such as antigorite (magnesium iron silicate hydroxide), clinochrysotile (magnesium silicate hydroxide), lizardite (magnesium silicate hydroxide), orthochrysotile (magnesium silicate hydroxide) and serpentine (iron magnesium silicate hydroxide); wickenburgite (hydrated lead calcium aluminum silicate); and zeophyllite (hydrated calcium silicate hydroxide fluoride).

In one preferred embodiment, the clay material is a phyllosilicate selected from the group consisting of clay minerals, kanemite, kenyaite, magadiite and makatite.

In another preferred embodiment, the phyllosilicate is a clay mineral, which is a group of phyllosilicates that contain a large percentage of water trapped between the silicate sheets. Most clay minerals are chemically and structurally analogous to other phyllosilicates but the larger amounts of water present, allow for more substitution of their cations.

Suitable clay minerals include chlorites such as baileychlore (zinc iron aluminum magnesium silicate hydroxide), chamosite (iron magnesium aluminum silicate hydroxide oxide), the generallized mineral chlorite, clinochlore (a chromium variety kaemmererite) (iron magnesium aluminum silicate hydroxide), cookeite (lithium aluminum silicate hydroxide), nimite (nickel magnesium iron aluminum silicate hydroxide), pennantite (manganese aluminum silicate hydroxide), penninite (iron magnesium aluminum silicate hydroxide) and sudoite (magnesium aluminum iron silicate hydroxide); glauconite (potassium sodium iron aluminum magnesium silicate hydroxide); illite (hydrated potassium aluminum magnesium iron silicate hydroxide); kaolinite (aluminum silicate hydroxide); montmorillonite (hydrated sodium calcium aluminum magnesium silicate hydroxide); palygorskite (hydrated magnesium aluminum silicate hydroxide); pyrophyllite (aluminum silicate hydroxide); sauconite (hydrated sodium zinc aluminum silicate hydroxide); talc (magnesium silicate hydroxide); and vermiculite (hydrated magnesium iron aluminum silicate hydroxide).

Swellable clay minerals are those that have alkali metals between their layers and can swell in polar solvents. These include lithium containing materials such as cookeite; sodium containing materials such as glauconite (which also contains potassium), montmorillonite and sauconite; and potassium containing materials such as illite. In some instances, such swellable materials are preferred over the non-swellable clay minerals.

It may be desirable to treat the phyllosilicate particles with an organic material to intercalate organic molecules between adjacent, planar silicate layers. For example, treatment can be with an organic material such as silane coupling agents; quaternary ammonium compounds; monomeric compounds having an electrostatic functionality selected from the group consisting of amines, amides and mixtures thereof; monomeric compounds having a functionality selected from the group consisting of hydroxyl, aromatic rings, carbonyl, carboxylic acid, polycarboxylic acid, aldehydes, ketones, amines, amides, ethers, esters and combinations thereof; an N-alkenyl amide monomer/allylic monomer combination, an oligomer formed by copolymerizing an N-alkenyl amide monomer and an allylic monomer, a polymer formed by copolymerizing an N-alkenyl amide monomer and an allylic monomer, and mixtures thereof, an intercalant polymer; and so forth.

In spite of some hydrophobization of the particle surface, such a treatment, for example by dioctadecyl ammonium chloride, leads to distinctive separation of clay platelets and their homogeneous distribution in polymer matrix. The reinforcing clay particles typically have an average diameter of about <15µ, and the average diameter is preferably within the range of about 2–6µ. Their thickness is around 10–100 nanometers and therefor can be referred to as nanoparticles, and the SCA is thus a "nanocomposite". Preferred clay particles are montmorillonite particles and are available from Southern Clay Products Co under the trademarks Cloisite Na+ (interspace length is 11.7), Cloisite 15A (interspace length is 31.5, clay modified with dioctylammoniumchloride to render it more hydrophobic), Cloisite 20A, and so forth.

G. Optional Additives

The adhesive may also include conventional additives such as adhesive agents, antioxidants, crosslinking or curing agents, pH regulators, pigments, dyes, refractive particles, conductive species, antimicrobial agents, active agents and permeation enhancers. In those embodiments wherein adhesion is to be reduced or eliminated, conventional detackifying agents may also be used. These additives, and amounts thereof, are selected in such a way that they do not significantly interfere with the desired chemical and physical properties of the adhesive.

Adhesive Agents

The skin-contacting adhesive of the invention can also include additional adhesive agents that serve to improve the adhesive and tack properties of the adhesive, which is particularly beneficial to maintain adhesiveness when the skin-contacting adhesive is used in a manner such that it is subjected to a large amount of mechanical stress. Exemplary materials include tacky rubbers such as polyisobutylene, polybutadiene, butyl rubber, polystyrene-isoprene copolymers, polystyrene-butadiene copolymers, and neoprene (polychloroprene). Preferred adhesive agents include low molecular weight polyisobutylene and butyl rubber.

In one embodiment, the hydrophobic pressure-sensitive adhesive material is added to the hydrophobic phase materials. A hydrophobic pressure-sensitive adhesive material such as PIB tends to have a low surface energy (30.5 $mJ/m^2$) compared with SIS (35.0 $mJ/m^2$) and the fresh SCA (32.5 $mJ/m^2$). Therefore, the PIB can readily migrate onto the patch surface. This migration can be accelerated by heating the patch, for example at 50° C. for 2 hours. After this treatment, the surface energy of formulation becomes equal to 30.7 $mJ/m^2$, i.e., close to PIB surface energy. Therefore, the inclusion of PIB in the contact zone with skin increases the initial tack.

A similar effect can be achieved by coating the patch surface with a dilute PIB solution in chloroform. After evaporation of solvent, the thin PIB layer forms reinforcing the initial tack without initiation of additional cold flow. Accordingly, the invention also contemplates coating the hydrophobic pressure-sensitive adhesive material onto the system and then heating the coating to remove any solvent and enable the material to diffuse into the system.

Antioxidants

The skin-contacting adhesive of the invention may also include one or more antioxidants. If used, the antioxidant is typically incorporated into the hydrophobic phase, and serves to enhance the oxidative stability of the composition. Heat, light, impurities, and other factors can all result in oxidation of the adhesive. Thus, ideally, antioxidants should protect against light-induced oxidation, chemically induced oxidation, and thermally induced oxidative degradation during processing and/or storage. Oxidative degradation, as will be appreciated by those in the art, involves generation of peroxy radicals, which in turn react with organic materials to form hydroperoxides. Primary antioxidants are peroxy free radical scavengers, while secondary antioxidants induce decomposition of hydroperoxides, and thus protect a material from degradation by hydroperoxides. Most primary antioxidants are sterically hindered phenols, and exemplary compounds for use herein are tetrakis [methylene (3,5-di-tert-butyl-4-hydroxyhydrocinnamate)] methane (e.g., Irganox®1010, from Ciba-Geigy Corp., Hawthorne, N.Y.) and 1,3,5-trimethyl-2,4,6-tris [3,5-di-t-butyl-4-hydroxy-benzyl] benzene (e.g., Ethanox®330, from Ethyl Corp.). Exemplary secondary antioxidants that may replace or supplement a primary antioxidant include tris(2,4-di-tert-butylphenyl) phosphite (e.g., Irgafos® 168, Ciba-Geigy Corp.). Other antioxidants, including but not limited to multi-functional antioxidants, are also useful herein and can serve as both a primary and a secondary antioxidant. Irganox®1520 D, manufactured by Ciba-Geigy is one example of a multifunctional antioxidant. Vitamin E antioxidants, such as that sold by Ciba-Geigy under the tradename Irganox®E17, are also useful in the present adhesives. Other suitable antioxidants include, without limitation, ascorbic acid, ascorbic palmitate, tocopherol acetate, propyl gallate, butylhydroxyanisole, butylated hydroxytoluene, bis(1,2,2,6,6-pentamethyl-4-piperidinyl)-(3,5-di-tert-butyl-4-hydroxybenzy l)butylpropanedioate, (available as Tinuvin®144 from Ciba-Geigy Corp.) or a combination of octadecyl 3,5-di-tert-butyl-4-hydroxyhydrocinnamate (also known as octadecyl 3-(3',5'-di-tert-butyl-4'-hydroxyphenyl)propionate) (available as Naugard®76 from Uniroyal Chemical Co., Middlebury, Conn.) and bis(1,2,2,6,6-pentamethyl-4-piperidinylsebacate) (available as Tinuvin®765 from Ciba-Geigy Corp.).

When included, the antioxidant can be present in amounts up to 2 wt % of the adhesive composition, but will typically be present in the range of about 0.05 wt % to 1.5 wt %.

pH Regulators

Compounds useful as pH regulators include, but are not limited to, glycerol buffers, citrate buffers, borate buffers, phosphate buffers and citric acid-phosphate buffers. These regulators may be included so as to ensure that the pH of the skin-contacting adhesive composition is compatible with that of an individual's body surface.

Pigments, Dyes and Refractive Particles

Pigments, dyes and refractive particles are typically included in an adhesive for aesthetic purposes, either to mimic the coloration of the skin surface or to provide an otherwise colorful adhesive.

There are numerous pigments and/or dyes that can be included in the include adhesive. Preferably such additives will not leach out and stain or otherwise irritate the skin surface. Refractive particles are particles that refract and reflect light striking the adhesive and the color of the reflected light changes as the angle at which the adhesive is viewed is changed. Exemplary refractive particles are those made from embossed, aluminized polyester.

Conductive Species

The skin-contacting adhesive may be rendered electrically conductive for use in biomedical electrodes and other electrotherapy contexts, i.e., to attach an electrode or other electrically conductive member to the body surface. For example, the adhesive may be used to attach a transcutaneous nerve stimulation electrode, an electrosurgical return electrode, or an EKG electrode to a patient's skin or mucosal tissue. Such applications generally involve modifying the adhesive composition so as to contain a conductive species, which renders the adhesive composition conductive. Suitable conductive species include those normally found in conductive adhesives used for application to the skin or other body surface, and include ionizable inorganic salts, organic compounds, or combinations of both. Examples of ionically conductive electrolytes include, by way of illustration and not limitation, ammonium sulfate, ammonium acetate, monoethanolamine acetate, diethanolamine acetate, sodium lactate, sodium citrate, magnesium acetate, magnesium sulfate, sodium acetate, calcium chloride, magnesium chloride, calcium sulfate, lithium chloride, lithium perchlorate, sodium citrate and potassium chloride, and redox couples such as a mixture of ferric and ferrous salts such as sulfates and gluconates, and combinations thereof. Although any amount of electrolyte may be present in the adhesive compositions of the invention, typically the electrolyte(s) will be present in an amount within the range of about 0.1–15 wt % of the adhesive.

Procedures for fabricating biomedical electrodes are well known in the art and can be readily adapted for incorporating the adhesive of the invention into such electrodes. See for example, U.S. Pat. No. 5,846,558 to Nielsen, et al., the disclosure of which is incorporated herein by reference with respect to manufacturing details.

Antimicrobial Agents

Antimicrobial agents may be included to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

Active Agents

One or more active agents can be included in the skin-contacting adhesive of the invention. Suitable active agents that may be incorporated into the adhesives of the invention, include the broad classes of compounds normally delivered through body surfaces and membranes such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof.

In a preferred embodiment, the active agent is selected from the group consisting of antibiotics, antifungal agents, antiinflammatory agents, bacteriostatic and bactericidal compounds, caustic agents, keratolytic agents, pain relieving agents, proteolytic enzymes, tissue-healing enhancing agents, vasodilators, vessicants, and combinations thereof.

Typically the active agent(s) will be present in a therapeutically effective amount. Examples of drugs within these classes are set forth below.

The release of active agents "loaded" into the adhesive of the invention typically involves both absorption of water and desorption of the agent via a swelling-controlled diffusion mechanism. Active agent-containing adhesives may be included in adhesive cushions, wound dressings, transdermal drug delivery devices and the like.

Antibiotics include antibiotics of the lincomycin family (referring to a class of antibiotic agents originally recovered from *streptomyces lincolnensis*); antibiotics of the tetracycline family (referring to a class of antibiotic agents originally recovered from *streptomyces aureofaciens*); sulfur-based antibiotics such as the sulfonamides; and so forth. Exemplary antibiotics of the lincomycin family include lincomycin itself (6,8-dideoxy-6-[[(1-methyl-4-propyl-2-pyrrolidinyl)-carbonyl]amino]-1-thio-L-threo-α-D-galacto-octopyranoside), clindamycin, the 7-deoxy, 7-chloro derivative of lincomycin (i.e., 7-chloro-6,7,8-trideoxy-6-[[(1-methyl-4-propyl-2-pyrrolidinyl) carbonyl]amino]-1-thio-L-threo-α-D-galacto-octopyranoside), and pharmacologically acceptable salts and esters thereof. Exemplary antibiotics of the tetracycline family include tetracycline itself 4-(dimethylamino)-1,4,4α,5,5α,6,11,12α-octahydro-3,6,12,12α-pentahydroxy-6-methyl-1,11-dioxo-2-naphthacenecarboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium.

Exemplary antifungal agents include chloroxylenol, ciclopirox, clotrimazole, griseofulvine, ketoconazole, miconazole, tolnaftate, undecylenic acid, and so forth.

Exemplary antiinflammatory agents include corticosteroids and nonsteroidal anti-inflammatory drugs. Examples of nonsteroidal anti-inflammatory drugs include alminoprofen, benoxaprofen, butibufen, carprofen, fenbufen, fenoprofen, flurbiprofen, ibuprofen, indoprofen, ketoprofen, naproxen, oxaprozin, pirprofen, pranoprofen, suprofen, tiaprofenic acid, and so forth.

Exemplary bacteriostatic and bactericidal compounds include, aryl mercury compounds such as phenylmercury borate or merbromin; alkyl mercury compounds such as thiomersal;chloramine; chlorohexidine; halogen compounds such as iodine, iodopovidone complexes (e.g., complexes of PVP and iodine, also referred to as "povidine" and available under the tradename Betadine® from Purdue Frederick); iodide salts; organic nitrogen compounds such as 8-hydroxyquinoline, chlorquinaldol, clioquinol, ethacridine, hexetidine, ehlorhexedine and ambazone; organotin compounds such as tri-n-butyltin benzoate; oxidants such as hydrogen peroxide and potassium permanganate; phenols such as thymol, o-phenyl phenol, 2-benzyl-4-chlorophenol, hexachlorophen and hexylresorcinol; silver and silver-containing compounds such as sulfadiazine, silver protein acetyltannate, silver nitrate, silver acetate, silver lactate, silver sulfate and silver chloride; sodium hypochlorite; zinc and zinc salts; and so forth.

Exemplary caustic agents include podophyllin, and the like.

Exemplary keratolytic agents include lactic acid, salicylic acid, urea, and so forth.

Exemplary pain relieving agents include local or topical anesthetics, including, but not limited to, acetamidoeugenol, alfadolone acetate, alfaxalone, amucaine, amolanone, amylocaine, benoxinate, betoxycaine, biphenamine, bupivacaine, burethamine, butacaine, butaben, butanilicaine, buthalital, butoxycaine, carticaine, 2-chloroprocaine, cinchocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, β-eucaine, euprocin, fenalcomine, fomocaine, hexobarbital, hexylcaine, hydroxydione, hydroxyprocaine, hydroxytetracaine, isobutyl p-aminobenzoate, kentamine, leucinocaine mesylate, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, zolamine, and the like, with tetracaine, lidocaine and prilocaine being particularly suitable herein.

Exemplary proteolytic enzymes include those agents that are effective wound cleansing agents, and include, for example, pepsin, trypsin, collagenase, chymotrypsin, elastase, carboxypeptidase, aminopeptidase, and the like.

Tissue-healing enhancing agents are also referred to in the art as tissue regenerative agents and include agents such as collagen; glycosaminoglycans such as hyaluronic acid, heparin, heparin sulfate and chondroitin sulfate; proteoglycans such as versican and biglycan; peptides such as fibronectin, vitronectin, osteopontin and thrombospondin, all of which contain the tripeptide sequence RGD (arginine-glycine-aspartic acid), a sequence generally associated with adhesive proteins and necessary for interaction with cell surface receptors; polypeptide growth factors such as platelet-derived growth factor, fibroblast growth factor, transforming growth factor and insulin-like growth factor; substrate adhesion molecules such as fibronectin, vitronectin and laminin; and so forth.

Exemplary vasodilators include those topical Vasodilators useful for increasing blood flow in the dermis, such as rubefacients and counterirritants. Rubefacient agents include nicotinic acid, nicotinates such as methyl, ethyl, butoxyethyl, phenethyl and thurfyl nicotinate, as well as the essential oils such as mustard, turpentine, cajuput and capsicum oil, and components thereof.

Exemplary vessicants include cantharidin, and the like.

Permeation Enhancers

One or more permeation enhancers can be included in the skin-contacting adhesive of the invention. With some active agents, it may be desirable to administer the agent along with a suitable permeation enhancer in order to achieve a therapeutically effective flux through the skin or mucosa. Selection of suitable permeation enhancers will depend upon the agent being delivered, as well as the enhancer's compatibility with the other components of the adhesive.

Exemplary permeation enhancers include, by way of illustration and not limitation, sulfoxides such as dimethylsulfoxide and decylmethylsulfoxide; ethers such as diethylene glycol monoethyl ether and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; the 1-substituted azacycloheptan-2-ones, particularly 1-n-dodecylcyclazacycloheptan- 2-one; alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid; and mixtures thereof.

H. Additional Elements

Backing Member

The skin-contacting adhesive of the invention may be formulated so as to include a backing member, which can be laminated to the adhesive layer to serve as the outer surface of a dressing, cushion or transdermal drug delivery device following application to the skin. Exemplary backing member materials include fibrous or porous sheet materials such as flannel, felt, cotton, polyesters, polyethylene, polypropylene, polyurethanes, polyether amides and the like. The backing member is typically along the order of about 1–2.5 mils in thickness, but may be thinker or thinner as needed. If desired, the backing can be pigmented, metallized, or provided with a matte finish suitable for writing.

In general, the material used for the backing layer should permit the skin-contacting adhesive to follow the contours of the skin and be worn comfortably on areas of skin such as at joints or other points of flexure, that are normally subjected to mechanical strain with little or no likelihood of the adhesive disengaging from the skin due to differences in the flexibility or resiliency of the skin and the adhesive.

Since the backing member covers a large surface area of the skin-contacting adhesive a highly water permeable backing can serve as a significant conduit for water to enter the adhesive. The combination of the degree of water permeability into the backing and the ability of the adhesive to hold water for a required period of wearing time needs to be in balance. Thus if the adhesive is designed to hold enough water from the skin and from the periphery of the adhesive and not lose its cohesive-adhesive properties during the required period of wearing time, then a water impermeable backing is suitable for use.

However if it is preferred to have some water leave the adhesive during wearing then a water or moisture permeable backing is preferred. In that instance, the amount of water intrusion into the adhesive and the moisture vapor transmission rate should be balanced. Also water should not be too soluble in the backing layer otherwise the backing layer may swell and either delaminate or cause the adhesive to lift-off prematurely. The outer surface of the backing ideally has a surface property that minimizes the ability of the adhesive to grab cloth normally used in socks, stockings or bed linen.

As noted above, when the adhesive is used in a dressing or cushion, the backing is preferably able to conform to the skin surface to which it is applied, for example, it can conform to the curvature of the ball and heel of a human foot when the foot is at rest. During walking or running there will be intermittent increased compression, tension and shear forces on the backing and the adhesive. Use of a flexible and/or elastic backing member, minimizes the occurrence of adhesive residue beyond the perimeter of the backing, which then would cause the dressing or cushion to stick to socks or bed coverings and possibly become detached from the skin surface. Thus the coefficient of friction, compression and other elastic properties of the backing are also important considerations.

In one embodiment of the invention, the backing is a polyurethane film having a thickness of about 1.5–2.0 mils. In another embodiment of the invention, the backing is a polymeric foam material. The porous nature of the foam can provide a depot of adhesive so that as pressure is applied to the skin-contacting adhesive, the adhesive formulation is continuously forced out of the pores to replenish the adhesive layer that is in contact with the skin.

Release Liner

The skin-contacting adhesive of the invention may be formulated so as to include a release liner, which can serve to protect the adhesive layer during storage and prior to use. The release liner preferably peels away with an easy peel and does not stick aggressively nor become difficult to remove from the adhesive during storage. Ideally, the release liner has adhesive properties that remain contact over time. The release liner can be made from numerous suitable materials, but is preferably differentiated from the adhesive, cushion, etc., by material texture or design and is impermeable to the adhesive composition. Exemplary release liners include silicone or fluorocarbon treated materials, polyesters, polyvinyl chloride, cellulose acetate, polypropylene, polyethylene and polyethylene terephthalate films. The release liner is typically along the order of about 3 mils in thickness, but may be thicker or thinner as needed.

Applicator Tab or Mechanism

The skin-contacting adhesive of the invention may be formulated so as to include an applicator tab or applicator mechanism, which is designed to facilitate application of the adhesive, cushion, etc., to the appropriate skin location. For example, an applicator tab can be a 2 mil polyolefin film.

III. CONFIGURATION AND SIZE

The skin contact area of the adhesive may be any size, but will typically be within in the range of about 3–250 $cm^2$, and preferably in the range of about 20–150 $cm^2$.

IV. FABRICATION

The skin-contacting adhesives of the invention are melt extrudable, and thus may be prepared using a simple blending and extruding process. The components of the adhesive are weighed out and then admixed, for example using a Brabender, Haake or Baker Perkins Blender, generally at a temperature within the range of about 90–160° C. Solvents may be added, but are not required. The resulting composition can be extruded using a single or twin-screw extruder. The composition can be extruded directly onto a substrate such as a backing member, covered with a release liner, and then pressed using, for example, a Carver press.

Figure 2:
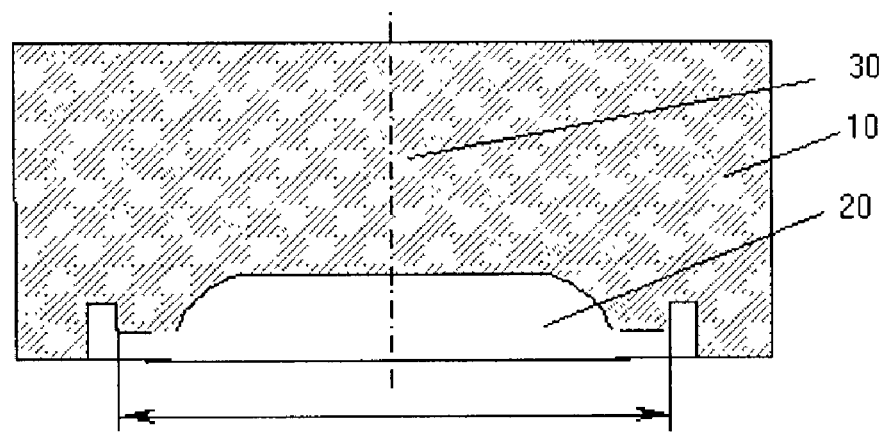
FIG. 2 is a punch suitable for processing the adhesives, cushions and wound dressings of the invention.

The thickness of the resulting skin-contacting adhesive, can have a variety of thicknesses, but typically will be in the range of about 0.20–0.80 mm, more usually in the range of about 0.30–0.5 mm. In a preferred embodiment, the SCA, wound dressing or patch has a tapered edge. FIG. 2 illustrates one type of tool that may be used to provide a tapered edges. The tool has a solid portion 10, which is typically metal, and a cut-out section 20 that is configured to match the desired dimensions of the adhesive, wound dressing or cushion to be shaped. Cutting lines are shown as 30. The extruded precursor of the product (e.g., a thin layer of SCA surrounded by backing film from one side and release liner from another side) passes through a set of such punches, where the precursor is pressed, profiled and cut out to provide a plurality of tapered-edge products.

The order in which the various ingredients may be added into the mixer is not critical to the invention, but in one preferred method the ingredients are added in the following order: tackifying resin, hydrophobic polymer, elastomeric plasticizer, any optional materials, the clay particles and finally the cellulose derived polymers. In another preferred method, two mixtures are prepared in advance and then mixed together with other components. Pellets of tackifier and hydrophobic polymers are premixed at ambient conditions (mixture "A"). Polysaccharide and clay are added to plasticizer and also premixed at room temperature (mixture "B"). Components can then be loaded into the mixer equipped with Benbary or sigma-blade rotors as follows:

| Time, min | Melt temperature, ° C. | Speed, rpm | Stage |
|---|---|---|---|
| 0 | >130 | 20–100 | Addition of mixture A |
| 1 | >130 | 20–100 | Stabilizer loaded |
| 20 | >130 | 20–100 | Cellulose derived polymers added |
| 40 | 130 | 20–100 | Temperature decrease started |
| 60 | <130 | 20–100 | Addition of mixture B |
| 80 | <130 | 20–100 | Additional agents introducing |
| 110 | <130 | 0 | End of mixing, discharge |

The temperature may be increased or decreased with each addition to facilitate manufacture or to control the product characteristics. For example cellulose derived polymers are melted with formation of anisotropic melt (130–140° C.). Triblock-copolymers as well as unsaturated polymers are softened in the same temperature range. Other component can be added at lower temperature to prevent their possible chemical decomposition. In this manner, the physical characteristics of the adhesive can be modified by altering the temperature regime, agitation speed and time.

The temperature profile can also be designed to provide for a desirable consistency of the SCA so that one is able to press the formed edge and to cut the desired wound dressing or cushion products. A suitable temperature for fabrication is around 70–110° C.

In one embodiment, the hydrophilic phase comprises at least one low molecular weight cellulose derived polymer and is formulated by (1) blending the hydrophobic polymer, elastomeric plasticizer, tackifying resin, and clay particles, to form a mixture; (2) heating the mixture to a temperature within the range of about 140–160° C.; and (3) adding the low and high molecular weight cellulose derived polymers to form a composition of the invention. One such process is exemplified as follows. The tackifying resin is first heated to 90–95° C. with slow mixing (about 20–30 rpm), the temperature is then elevated to 95–105° C. and the hydrophobic polymer added, with slow mixing (about 20–30 rpm). The temperature is then raised to about 140–160° C. to obtain a homogenous melt prior to addition of the elastomeric plasticizer, which is then added with slow or rapid mixing (about 20–100 rpm). While maintaining this temperature, any optional materials and the clay particles can be added with rapid mixing. The mixture is then maintained or cooled (if needed) to reach a temperature of about 135–150° C. and the low and high molecular weight cellulose derived polymers are added with rapid mixing.

In another embodiment, the hydrophilic phase comprises at least one naturally occurring polysaccharide and is formulated by (1) pre-mixing the tackifying resin and hydrophobic polymer to form a first mixture; (2) pre-mixing the polysaccharide, clay particles, elastomeric plasticizer to form a second mixture; (3) heating the first mixture to a temperature within the range of about 140–160° C.; (4) adding the high molecular weight cellulose derived polymer to the first mixture; (5) cooling the first mixture; and (6) adding the second mixture to the first mixture to form a composition of the invention. One such process is exemplified as follows. The tackifying resin and hydrophobic polymer are pre-mixed at ambient temperature. The polysaccharide, clay particles, elastomeric plasticizer are also premixed at ambient temperature. The resin/polymer mixture is then heated to 140–160° C. with slow mixing. Optional ingredients may also be added at this point, for example an antioxidant, while maintaining the same temperature and speed. The high molecular weight cellulose derived polymer is then added, while maintaining the same temperature and speed. The mixture is then cooled to about 110–130° C. and the clay mixture is added. Optional ingredients, for example an adhesive agent, can also be added after the clay mixture.

Additional details of suitable mixing procedures are also described in the Examples.

V. SPECIFIC USES

The skin-contacting adhesive compositions of the invention find utility in numerous applications, such as in transdermal drug delivery devices, topical and transdermal pharmaceutical formulations, pressure-relieving cushions (which may or may not be medicated), bandages, ostomy devices, prosthesis securing means, face masks, sound, vibration or impact absorbing materials, and the like. Also, the compositions may be rendered electrically conductive by incorporation of an electrically conductive material, and may thus be used for attaching an electroconductive particle, such as an electrode (e.g., a transcutaneous electric nerve stimulation electrode, an electrosurgical return electrode or an EKG monitoring electrode), to an individual's body surface.

The skin-contacting adhesive compositions provide several significant advantages, including:
(1) fabricated so as to be translucent, which enables one to view the extent of wound healing without removing the hydrogel from the body surface;
(2) displays of very high swelling upon contact with water;
(3) exhibits little or no cold flow during use; and
(4) readily modified during manufacture so that properties such as adhesion, absorption, and translucence can be optimized.

A. Adhesive Cushion

The skin-contacting adhesive compositions of the invention are useful in any number of applications wherein adhesion of a product to a body surface is called for or is desirable. One such embodiment is an adhesive cushion which comprises (a) a skin-contacting layer of an adhesive composition comprised of a hydrophobic phase and a hydrophilic phase and (b) a backing layer. The hydrophobic and hydrophilic phases are as described above.

The backing layer is preferably non-occlusive (or "breathable"), i.e., is preferably permeable to moisture and will generally be made of a flexible, resilient outer layer, fabricated from a translucent or transparent, film, a foam pad or fibrous material such as fabric, with a layer of the adhesive composition of the invention laminated thereto for application to the skin surface. Exemplary backing players include transparent polyurethane, transparent polyurethane coated with acrylic adhesive (to reinforce the connection between SCA and backing layer and foamed polyurethane. Use of foamed or fabric backings may provide for increased cushioning, however, use of such as backing will decrease the transparency properties of the product. When moisture permeability is particularly preferred, the backing layer should provide for anisotropic moisture transportation, i.e., from the skin through the SCA and the backing member, and then to the environment, but not vice versa, for example during bathing.

Suitable cushions include, arch support pads, blister pads, bunion pads, callus pads, corn pads, elbow pads, finger pads, forearm pads, heel cushions, insoles, knee pads, metatarsal pads, shin pads, toe pads, wrist pads, and so forth. Preferably, the adhesive cushion stays affixed to the skin for at least seventy-two hours.

The adhesive cushion may further comprise a therapeutically effective amount of an active agent, as defined above. In particular, active agents such as bacteriostatic and bactericidal compounds and antibiotic agents, and combinations thereof may be included in the adhesive composition.

The adhesive cushion can have a skin-contacting area in the range of about 3–250 cm$^2$, typically about 3–10 cm$^2$. A common shape for adhesive callus cushions is circular, and such patches will typically have a diameter within the range of about 3.15–3.50 cm. Blister, bunion and corn cushions typically have an elliptic shape with tapered edges of different dimensions.

The adhesive cushion finds particular utility as pressure-relieving cushion for application to a foot. In one such embodiment, the cushion contains an active agent for the treatment of dicubitis, venous and diabetic foot ulcers, or the like.

B. Wound Dressings

For wound dressings, suitable active agents are those useful for the treatment of wounds, and include, but are not limited to antibiotics, antifungal agents, antiinflammatory agents, bacteriostatic and bactericidal compounds, pain relieving agents, proteolytic enzymes, tissue-healing enhancing agents, vasodilators, and combination thereof. Specific agents within these classes are set above.

In one embodiment, the wound dressing comprises a laminated composite of a body facing layer having a body-contacting surface, and an outwardly facing non-occlusive backing layer, wherein at least a portion of the body-contacting surface is comprised of a skin-contacting adhesive comprised of a hydrophobic phase and a hydrophilic phase. The hydrophobic and hydrophilic phases are as described above.

The wound dressing can be designed such that the entire body-contacting surface is comprised of the adhesive, or the perimeter can be made up of the adhesive with an inner wound-contacting region made of a material such as a hydrogel.

The wound dressing may further include a backing layer and a removable release liner that covers and is co-extensive with the body-facing surface of the wound dressing.

It may be desirable to prepare the adhesive composition so that it is substantially nontacky, or at most slightly tacky, when applied to the body surface. In addition, the adhesive composition may further comprise a therapeutically effective amount of an active agent, as defined above, that is suitable for application to a wound. In particular, active agents such as antibiotics, antifungal agents, antiinflammatory agents, bacteriostatic and bactericidal compounds, pain relieving agents, proteolytic enzymes, tissue-healing enhancing agents, vasodilators, and combination thereof may be included in the adhesive composition.

A typical skin-contacting area in the range of about 3–250 cm$^2$, typically about 3–10 cm$^2$. Wound dressings are often rectangular in shape, and are commonly as large as 250 cm$^2$.

C. Transdermal Drug Delivery Devices

The skin-contacting adhesive composition also find utility when incorporated into a transdermal drug delivery device. In one embodiment, such a device is comprised of a drug reservoir containing a therapeutically effective amount of an active agent, an outwardly facing backing layer, and a means for affixing the device to a body surface comprising a skin-contacting adhesive composition comprised of a hydrophobic phase and a hydrophilic phase, as described above.

In the manufacture of such transdermal or transmucosal drug delivery devices, the skin-contacting adhesive composition may be cast or extruded onto a backing layer or release liner of such a device and will serve as the skin contacting face of the "patch." The drug reservoir may be separate from the adhesive composition or the adhesive itself may be serve as a drug reservoir within the device.

Any number of active agents can be administered using these drug delivery devices of the invention. The device will contain a quantity of a pharmacologically active agent effective to provide the desired dosage over a predetermined delivery period and may also contain a carrier (e.g., a vehicle to solubilize the active agent), a permeation enhancer, if necessary, and optional excipients such as colorants, thickening agents, stabilizers, surfactants and the like.

The transdermal drug delivery device may also contain a release liner or a rate-controlling membrane formed of a material selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, polysiloxane-polycarbonate block copolymer and the like.

D. Other Products Requiring Adhesion To The Skin

The skin-contacting adhesive compositions of the invention are also useful in a host of other contexts, e.g., as adhesives for affixing medical devices, diagnostic systems and other devices to be affixed to a body surface, and in any other application wherein adhesion to a body surface is necessary or desired. The adhesive compositions are also useful as sealants for ostomy devices, prostheses, and face masks, as sound, vibration or impact absorbing materials, as carriers in cosmetic and cosmeceutical gel products, and will have other uses known to or ascertainable by those of ordinary skill in the art, or as yet undiscovered.

The practice of the present invention will employ, unless otherwise indicated, conventional techniques of polymer chemistry, adhesive manufacture, and hydrogel preparation, which are within the skill of the art. Such techniques are fully explained in the literature.

EXAMPLES

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

ABBREVIATIONS AND TRADEMARKS

The following abbreviations and tradenames are used in the examples:

| | |
|---|---|
| Adhesive Agent | Low molecular weight polyisobutylene rubber |
| APFR | Alkylphenolformaldehyde resin SP 1055 |
| BR 065 | High molecular weight butyl rubber (Exxon) |
| DCP | Dicumyl peroxide |
| Cloisite Na$^+$ | Natural clay (Southern Clay Products) |
| Cloisite 15A | Natural clay modified with dioctadecylammonium (Southern Clay Products) |
| Escorez 5380 | Hydrocarbon resin (Exxon) |
| GF | HPC polymer (available under the tradename Klucel ®, Hercules Inc.); molecular weight of about 370,000 g/mole |
| HF | HPC polymer (Klucel ®); molecular weight of about 1,150,000 g/mole |
| HPC | Hydroxypropylcellulose |
| HPMC | Hydroxypropylmethylcellulose |
| Irganox ® 1010 | Antioxidant, Tetrakis [methylene (3,5-di-tert-butyl-4-hydroxyhydrocinnamate)] methane (Ciba-Geigy) |
| Isolene ® 400 | Cis-1,4 polyisoprene (Elementis Specialties Performance Polymers) |
| Kalene 1300 | Low molecular weight butyl rubber (Elementis Specialties Performance Polymers) |
| LF | HPC polymer (Klucel ®); molecular weight of about 80,000–95,000 g/mole |
| JF | HPC polymer (Klucel ®); molecular weight of about 140,000 g/mole |
| MF | HPC polymer (Klucel ®); molecular weight of about 850,000 g/mole |
| Na—CMC | Sodium carboxymethylcellulose |
| Natsyn ® 2210 | Polyisoprene rubber (Goodyear Tire and Rubber) |
| Paraffin oil | Oil extender |
| PIB | Polyisobutylene |
| PFR | Phenolformaldehyde resin |
| Regalite ® 9100 | Partially hydrogenated hydrocarbon resin (Hercules) |
| Styrene plasticizer | Styrene-isoprene copolymer (Kraton) |
| Vector 4111 | Styrene-isoprene-styrene block copolymer (available from Dexco Polymers); styrene:isoprene ratio of 18:82) |
| Vector 4114 | Styrene-isoprene-styrene block copolymer (Dexco Polymers); 42 wt % styrene-isoprene diblock; overall styrene:isoprene ratio of 15:85 |
| Wingtack 86 | Synthetic polyterpene resin (Goodyear Tire and Rubber) |

Example 1

The following are exemplary formulations of skin-contacting adhesive of the invention. The prepared formulations were all translucent, as determined visually.

The manufacture of Formulations 1 and 2 involved adding the cellulose derived polymers at a high temperature (>130° C.). In this manner, the polymers are melted, forming liquid crystalline droplets, which are stretched at mixing giving fibers (high MW cellulose derived polymer) or ellipsoids (low MW cellulose derived polymer).

| Ingredient | Wt % |
|---|---|
| Formulation 1 | |
| Hydrophobic polymer: Vector 4111 | 44.69 |
| Elastomeric plasticizer: Styrene plasticizer | 28.86 |
| Tackifying resin: Regalite ® 9100 | 1.86 |
| High MW Cellulose derived polymer: MF | 9.31 |
| Low MW Cellulose derived polymer: LF | 9.31 |
| Clay particles: Cloisite Na+ | 5.6 |
| Other ingredients: Irganox ® 1010 | 0.37 |
| Formulation 2 | |
| Hydrophobic polymer: Vector 4111 | 45.11 |
| Elastomeric plasticizer: Styrene plasticizer | 30.07 |
| Tackifying resin: Regalite ® 9100 | 1.88 |
| High MW Cellulose derived polymer: MF | 9.40 |
| Low MW Cellulose derived polymer: HPMC | 9.40 |
| Clay particles: Cloisite 15A | 3.76 |
| Other ingredients: Irganox ® 1010 | 0.37 |

Water Uptake Studies

A water uptake study was conducted on skin-contacting adhesives prepared in Example 1 and the swell ratio and water uptake were calculated.

Procedure: Each skin-contacting adhesive was die-cut into circles 25 mm in diameter. The cross-sectional area of the adhesive was measured using a ruler while the thickness of the patch was determined using a Mitotoyo Digimatic Micrometer at three points across the sample. The weight of the dry adhesive samples was also determined using a 5-decimal point microbalance. Each sample was then immersed in 20 ml of phosphate-buffered saline (0.9% w/v, 0.1M phosphate buffer pH 7.40) at 37° C. The weight and dimensions of each swollen adhesive sample were determined after 24 hours water uptake, after dabbing off excess solution. The weight difference represents the amount of water imbibed by the material. The samples were dried at 90° C. for 2 to 4 hours before taking their weight and dimensions to obtain the degree of dissolution of the patch. Each experiment was repeated three times, and the indicated values are averages. Results are set forth below.

| Formulation | % Water Uptake | Swell Ratio |
|---|---|---|
| Formulation 1 | 96.15 | 1.46 |
| Formulation 2 | 48.6 | 1.21 |

Tack Studies

Tack studies were conducted and the probe tack measurements were provided from a stainless steel probe having a diameter of approximately 0.5 cm using the following conditions: applied contact weight of 177 g, dwell time of 10 seconds, withdrawal speed of 5.0 cm/sec.

Results are set forth below.

| | Tack (g) | |
|---|---|---|
| Formulation | 0.2 cm/sec | 0.01 cm/sec |
| Formulation 1 | 340 | 120 |
| Formulation 2 | 284.3 | 102.3 |

Example 2

The following is another exemplary formulation of the skin-contacting adhesive of the invention. The prepared formulation was translucent, as determined visually.

The manufacture of Formulation 3 involved adding the cellulose derived polymers at a lower temperature (about 100° C). In this manner, the polymers behaved like a powder.

| Formulation 3 | |
|---|---|
| Ingredient | Wt % |
| Hydrophobic polymer: Vector 4111 | 45.54 |
| Elastomeric plasticizer: Styrene plasticizer | 29.41 |
| Tackifying resin: Regalite ® 9100 | 1.9 |
| High MW Cellulose derived polymer: MF | 9.49 |
| Low MW Cellulose derived polymer: LF | 9.49 |
| Clay particles: Cloisite Na+ | 3.8 |
| Other ingredients: Irganox ® 1010 | 0.38 |

Water Uptake Studies

A water uptake study of Formulation 3 was conducted as described in Example 1. The percentage water uptake was 35.6, with a swell ratio of 1.22

Tack Studies

A tack study was conducted as described in Example 1. Formulation 3 had a tack of 375.7 g at 0.2 cm/sec and 142.3 g at 0.01 cm/sec.

Example 3

The following is an additional exemplary formulation of the skin-contacting adhesive of the invention. The prepared formulation was translucent, as determined visually.

The manufacture of Formulation 4 involved adding the cellulose derived polymers at a high temperature (above 130° C.) so the polymers behaved like liquid crystals.

| Formulation 4 | |
|---|---|
| Ingredient | Wt % (temp/rpm) |
| Tackifying resin: Regalite ® 9100 | 27.97 (94/23) |
| Hydrophobic polymer: Vector 4111 | 9.57 (100/23) |
| Hydrophobic polymer: Vector 4114 | 9.54 (101/23) |
| Elastomeric plasticizer: Styrene plasticizer | 14.5 (151/31) |
| Other: Adhesive Agent | 1.5 (150/58) |
| Clay particles: Cloisite Na+ | 3.0 (144/100) |
| Low MW Cellulose derived polymer: JF | 11.97 (140/100) |

-continued

Formulation 4

| Ingredient | Wt % (temp/rpm) |
|---|---|
| High MW Cellulose derived polymer: GF | 17.95 (144/100) |
| High MW Cellulose derived polymer: HF | 4.0 (146/100) |

The ingredients are listed in the order in which they were added to the mixture. "Temp" refers to the temperature (° C.) of the mixture or melt when the particular ingredient was added, while "rpm" refers to the revolutions per minute of the mixture when the particular ingredient was added. Such temperatures and rpm values were maintained until the next ingredient was added.

After the final addition of clay particles, mixing was continued for 15 minutes at the final temperature of 144° C., and for 3 minutes at 150° C.

Tack Studies

Tack studies were conducted on Formulation 4 as described in Example 1. The speed was 0.2 cm/sec with a 10 second dwell time. Results are set forth below.

| Sample # | Sample thickness (mil) | Tack (g) |
|---|---|---|
| 1 | 23.0 | 605 |
| 2 | 24.5 | 616 |
| 3 | 25.0 | 797 |
| Average | 24.16 | 672.66 |
| % RSD | 4.31 | 16.0 |

Example 4

The following is an additional exemplary formulation of the skin-contacting adhesive of the invention. The prepared formulation was translucent, as determined visually.

The manufacture of Formulation 5 involved adding the cellulose derived polymers at a high temperature (above 130° C.) so the polymers behaved like liquid crystals.

Formulation 5

| Ingredient | Wt (g) | Temp | rpm | Wt % |
|---|---|---|---|---|
| Tackifying resin: Regalite ® 9100 | 15.5 | 94 | 20 | 28.1 |
| Hydrophobic polymer: Vector 4111 | 5.25 | 100 | 20 | 9.51 |
| Hydrophobic polymer: Vector 4114 | 5.25 | 101 | 20 | 9.51 |
| Elastomeric plasticizer: Styrene plasticizer | 4.0 | 148 | 20 | 7.25 |
| Elastomeric plasticizer: Isolene ® 400 | 4.0 | 146 | 20 | 7.25 |
| Other: Adhesive Agent | 0.833 | 138–140 | 20–100 | 1.51 |
| Clay particles: Cloisite Na⁺ | 1.65 | 144 | 100 | 2.99 |
| Low MW Cellulose derived polymer: JF | 6.6 | 138–140 | 100 | 11.96 |
| High MW Cellulose derived polymer: GF | 9.9 | 144 | 100 | 17.94 |
| High MW Cellulose derived polymer: HF | 2.2 | 146 | 100 | 3.98 |

The ingredients are listed in the order in which they were added to the mixture. "Temp" refers to the temperature (° C.) of the mixture or melt when the particular ingredient was added, while "rpm" refers to the revolutions per second of the mixture when the particular ingredient was added. Such temperatures and rpm values were maintained until the next ingredient was added. After the final addition of clay particles, mixing was continued for 15 minutes at the final temperature of 146° C.

Tack Studies

Tack studies were conducted as described in Example 1. The speed was 0.2 cm/sec with a 10 second dwell time. Results are set forth below.

| Sample # | Sample thickness (mil) | Tack (g) |
|---|---|---|
| 1 | 17.5 | 656 |
| 2 | 20.5 | 614 |
| 3 | 19.5 | 519 |
| Average | 19.16 | 596.3 |
| % RSD | 7.97 | 11.7 |

Example 5

The following Formulations 6–8 are additional exemplary formulations of the skin-contacting adhesive of the invention.

Formulation

| Ingredient | 6 Wt % | 7 Wt % | 8 Wt % |
|---|---|---|---|
| Hydrophobic polymer: Vector 4111 | 20.0 | 19.1 | 18.0 |
| Tackifying resin: Regalite ® 9100 | 29.5 | 28.1 | — |
| Tackifying resin: Escorez 5380 | — | — | 35.0 |
| Elastomeric plasticizer: Styrene plasticizer | 15.0 | 14.3 | 10.0 |
| Other: Adhesive Agent | 1.5 | 1.5 | — |
| Clay particles: Cloisite Na⁺ | 4.0 | 3.0 | 3.0 |
| Low MW Cellulose derived polymer: JF | 12.0 | 12.0 | 12.0 |
| High MW Cellulose derived polymer: GF | 18.0 | 18.0 | 18.0 |
| High MW Cellulose derived polymer: HF | — | 4.0 | 4.0 |

The adhesive strength of these formulations was measured and determined to be 650 ±20 N/m, 800±20 N/m, and 450÷500 N/m for Formulations 8, 9 and 10, respectively.

Example 6

The following Formulations 9–13 are additional exemplary formulations of the skin-contacting adhesive of the invention.

Formulation

| Ingredient | 9 Wt % | 10 Wt % | 11 Wt % | 12 Wt % | 13 Wt % |
|---|---|---|---|---|---|
| Hydrophobic polymer: Vector 4114 | 20.0 | 20.0 | — | 20.0 | 18.0 |
| Hydrophobic polymer: Vector 4111 | — | — | 21.0 | — | — |
| Tackifying resin: Regalite ® 9100 | 25.5 | 25.5 | — | 25.5 | 25.5 |
| Tackifying resin: Escorez 5380 | — | — | 30.0 | — | — |
| Elastomeric plasticizer: Isolene ® 400 | 5.0 | 10.0 | 10.0 | 15.0 | 15.0 |
| Elastomeric plasticizer: Styrene plasticizer | — | 5.0 | — | — | — |
| Other: Adhesive Agent | 1.5 | 1.5 | — | 1.5 | 1.5 |
| Clay particles: Cloisite Na⁺ | 8.0 | 8.0 | 4.0 | 10.0 | 20.0 |
| High MW Cellulose derived polymer: GF | — | — | — | 5.0 | 10.0 |

-continued

| | Formulation | | | | |
|---|---|---|---|---|---|
| Ingredient | 9 Wt % | 10 Wt % | 11 Wt % | 12 Wt % | 13 Wt % |
| Naturally occurring polysaccharide: Agar | 15.0 | 15.0 | — | 20.0 | 5.0 |
| Naturally occurring polysaccharide: Starch | — | — | 20.0 | — | — |
| Other: Paraffin oil | — | — | 5.0 | — | — |
| High MW Cellulose derived polymer: MF | 15.0 | 12.0 | 10.0 | — | — |
| Low MW Cellulose derived polymer: LF | 10.0 | 3.0 | — | 3.0 | 5.0 |
| Other: Irganox ® 1010 | ~0.1 | ~0.1 | ~0.1 | ~0.1 | ~0.1 |

The ingredients in the table below are listed in the order in which they were added to the mixture. Pellets of Regalite®9100 and Vector 4114 were premixed at ambient temperature to form "Mixture A". Agar and the clay particles were added to polyisoprene and styrene plasticizers, and premixed at ambient temperature to form "Mixture B".

| Ingredient | Temp | rpm |
|---|---|---|
| Mixture A | 150 | 30 |
| GF, MF or LF | 150 | 30 |
| Mixture B | 120 | 30 |
| Adhesive Agent | 120 | 30 |

"Temp" refers to the temperature (° C.) of the mixture or melt when the particular ingredient was added, while "rpm" refers to the revolutions per minute of the mixture when the particular ingredient was added. Such temperatures and rpm values were maintained until the next ingredient was added, except that the temperature was raised to 120° C. after the addition of GF. After the final addition of clay particles, mixing was continued for 30 minutes at the final temperature of 120° C.

Formulations 9–13 were tested for water uptake, moisture penetration rate, adhesion (peel and tack testers), as well as their wearing properties as callus, corn, and bunion cushions. The wearing results of various groups of people for callus cushion are presented below.

| Formulation | Number of Volunteers* | Avg. number of showers | Avg. wearing time, hours |
|---|---|---|---|
| 9 | 3-MY | 2.7 | 69.3 |
| | 4-MO | 3.5 | 85.2 |
| | 3-FY | 2.9 | 70.3 |
| | 2-FO | 3.2 | 74.5 |
| 10 | 2-MY | 3.0 | 70.5 |
| | 3-MO | 3.3 | 75.3 |
| | 3-FY | 2.3 | 52.3 |
| | 3-FO | 3.3 | 73.3 |
| 11 | 3-MY | 2.3 | 62.0 |
| | 4-MO | 2.0 | 48.0 |
| | 2-FY | 1.5 | 44.5 |
| | 4-FO | 1.8 | 48.2 |
| 12 | 3-MY | 3.0 | 72.0 |
| | 3-MO | 3.0 | 74.0 |
| | 3-FY | 2.7 | 68.3 |
| | 4-FO | 3.2 | 78.2 |
| 13 | 2-MY | 2.5 | 58.5 |
| | 4-MO | 2.7 | 66.2 |
| | 3-FY | 2.3 | 52.3 |
| | 2-FO | 2.7 | 63.5 |

*M = male volunteer
F = female volunteer
Y = younger than 35 years of age
O = older than 35 years of age Example 7

This example describes using unsaturated elastomers accompanied by plasticizers, tackifiers, oil extender and curing agents as hydrophobic phase, and various cellulose derivatives in the hydrophilic phase. The following Formulations 14–18 are additional exemplary formulations of the skin-contacting adhesive of the invention.

| | Formulation | | | | |
|---|---|---|---|---|---|
| Ingredient | 14 Wt % | 15 Wt % | 16 Wt % | 17 Wt % | 18 Wt % |
| Hydrophobic polymer: BR 065 | — | 30.0 | 30.0 | 22.0 | — |
| Elastomeric plasticizer: Kalene 1300 | — | 20.0 | 27.0 | — | — |
| Elastomeric plasticizer: PIB | — | — | — | 25.0 | — |
| Hydrophobic polymer: Natsyn ® 2210 | 20.0 | — | — | — | 25.6 |
| Elastomeric plasticizer: Isolene ® 400 | 15.0 | — | — | — | 17.1 |
| Tackifying resin: Regalite | — | 12.0 | 10.0 | 13.5 | 21.3 |
| Tackifying resin: Wingstack 86 | 15.0 | — | — | — | — |
| High MW Cellulose derived polymer: Na-CMC | 20.0 | — | 22.0 | — | — |
| Other: PFR Curing Agent | — | 4.0 | — | 4.5 | — |
| Other: APFR Curing Agent | — | 3.0 | 3.0 | — | — |
| Other: DCP Curing Agent | 5.0 | — | — | — | 2.0 |
| Other: Paraffin oil | 5.0 | — | — | — | — |
| Low MW Cellulose derived polymer: LF | — | 13.0 | 5.0 | — | 12.0 |
| Low MW Cellulose derived polymer: JF | 16.0 | — | — | 17.0 | — |
| High MW Cellulose derived polymer: GF | — | — | — | — | 14.0 |
| High MW Cellulose derived polymer: MF | — | 10.0 | — | — | — |
| High MW Cellulose derived polymer: HF | — | 3.0 | — | 15.0 | 4.0 |
| Clay particles: Cloisite 15A | 4.0 | 5.0 | 3.0 | 3.0 | 4.0 |

Figure 3:
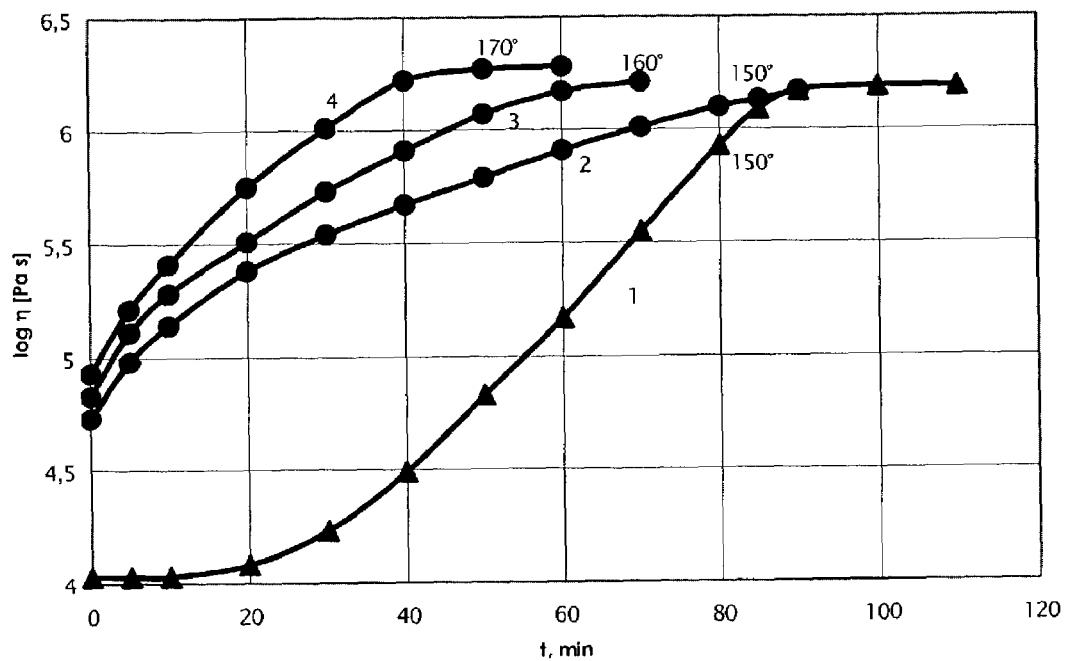
FIG. 3 is a rheokinetic curve for the precursor for formulation 17 and the complete formulation 17 of Example 7.

In order to effectively apply these formulations to locations on the body that are subjected to constant or varying pressure, it is preferable to select a curing regime (content of crosslinker, time, temperature) that will diminish cold flow. The measurement of the change in viscosity over time provides a useful and informative estimation of curing kinetics. As an example, rheokinetic curves for the precursor of formulation 17 (BR/PIB/Regalite+4.5% APFR) at 150° C. (Curve 1) and for the complete formulation 17 at 150° C. (Curve 2), 160° C. (Curve 3) and 170° C. (Curve 4), as shown in FIG. 3. Curve 1 shows that there is an induction period, a region of sharp viscosity increase, and a plateau region. It is believed that the plateau region corresponds to the maximum attainable at the given conditions of the density of the chemical network. Introducing the hydrophilic cellulose derived polymers leads to the disappearance of the induction period (Curve 2). An increase of curing temperature to 160° C. (Curve 3) and 170° C. (Curve 4) results in reducing the time to reach the plateau region from 80 to 40 min.

Figure 4:
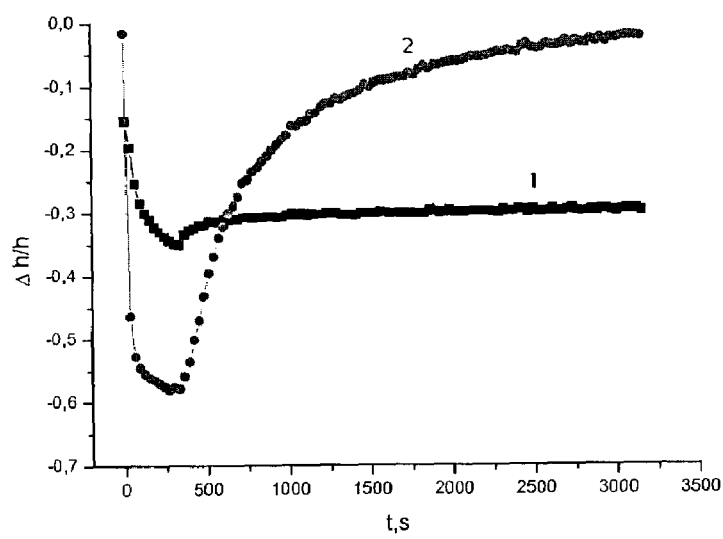
FIG. 4 presents the results of squeeze-recoil tests conducted on formulation 17 of Example 7.

The squeeze-recoil method provides useful information as to the absence of any cold flow. According to this method, a flat sample is squeezed under constant force for a set time, the force is removed and the elastic recovery of the sample measured. Two sets of squeeze-recoil curves are shown in FIG. 4. Curve 1 describes the elastic properties of formulation 17, cured for 40 minutes at 150° C. Curve 2 describes the elastic properties of formulation 17, cured for 40 minutes at 170° C. The elastic recovery reaches ~40% at 150° C. and >90% at 170° C. Using this method, it is therefore possible to estimate the optimal curing conditions.

In another embodiment of the invention, the hydrophobic phase can be cured by means of UV irradiation. The curing kinetics can the be readily measured by standard swelling techniques, and the completeness of the curing process can be measured by the squeeze-recoil method.

Formulations 14–18 were characterized by water uptake, initial tack, adhesion, and wearing properties. All exhibited properties that would render them suitable for use as wound dressings and cushion products. In addition, the formulations containing a polyisoprene elastomeric plasticizer (Natsyn® 2210 or Isolene® 400) maintained their transparency even after water uptake test.

All patents, patent applications, journal articles and other references cited herein are incorporated by reference in their entireties.

It is to be understood that while the invention has been described in conjunction with the preferred specific embodiments hereof, the foregoing description, as well as the examples which are intended to illustrate and not limit the scope of the invention, it should be understood by those skilled in the art that various changes may be made and equivalents may be substituted without departing from the scope of the invention. Other aspects, advantages and modifications will be apparent to those skilled in the art to which the invention pertains.

Accordingly, the scope of the invention should therefore be determined with reference to the appended claims, along with the full range of equivalents to which those claims are entitled.

We claim:

1. A skin-contacting adhesive composition comprised of a hydrophobic phase and a hydrophilic phase, wherein:
    (a) the hydrophobic phase comprises a hydrophobic polymer, at least one elastomeric plasticizer and a tackifying resin; and
    (b) the hydrophilic phase comprises:
        i) at least one material selected from the group consisting of low molecular weight cellulose derived polymers and naturally occurring polysaccharides;
        ii) at least one high molecular weight cellulose derived polymer; and
        iii) reinforcing clay particles.

2. The composition of claim 1 which comprises about 50–80 wt % hydrophobic phase and about 20–50 wt % hydrophilic phase.

3. The composition of claim 2 which comprises about 60–70 wt % hydrophobic phase and about 30–40 wt % hydrophilic phase.

4. The composition of claim 1 which comprises about 10–50 wt % hydrophobic polymer; about 5–40 wt % elastomeric plasticizer; about 0.5–40 wt % tackifying resin; about 5–40 wt % high molecular weight cellulose derived polymers; about 2–30 wt % reinforcing clay particles; and about 0–20 wt % optional ingredients.

5. The composition of claim 4 which comprises about 15–46 wt % hydrophobic polymer; about 5–31 wt % elastomeric plasticizer; about 1–35 wt % tackifying resin; and about 5–32 wt % high molecular weight cellulose derived polymers; about 3–20 wt % reinforcing clay particles; and about 0.1–10 wt % optional ingredients.

6. The composition of claim 4 which comprises about 2–40 wt % naturally occurring polysaccharides.

7. The composition of claim 6 which comprises about 5–20 wt % naturally occurring polysaccharides.

8. The composition of claim 4 which comprises about 1–20 wt % low molecular weight cellulose derived polymers.

9. The composition of claim 8 which comprises about 3–17 wt % low molecular weight cellulose derived polymers.

10. The composition of claim 1 wherein the weight ratio of the hydrophobic phase and the hydrophilic phase is selected so as to optimize the adhesive strength, cohesive strength and water sorption of the composition.

11. The composition of claim 1 wherein the weight ratio of the high molecular weight cellulose derived polymers, low molecular weight cellulose derived polymers or naturally occurring polysaccharides, and the reinforcing clay particles is selected so as to optimize the adhesive strength, cohesive strength and water sorption of the composition.

12. The composition of claim 1 wherein the weight ratio of the hydrophobic polymer, elastomeric plasticizer and tackifying resin is selected so as to optimize the adhesive strength, cohesive strength and water sorption of the composition.

13. The composition of claim 1 wherein the weight ratio of the hydrophobic phase and the hydrophilic phase is selected so as to render the composition translucent.

14. The composition of claim 1 wherein the weight ratio of the high molecular weight cellulose derived polymers, low molecular weight cellulose derived polymers, naturally occurring polysaccharides, and the reinforcing clay particles is selected so as to render the composition translucent.

15. The composition of claim 1 wherein the weight ratio of the hydrophobic polymer, elastomeric plasticizer and tackifying resin is selected so as to render the composition translucent.

16. The composition of claim 1 wherein the hydrophobic polymer is selected from the group consisting of butadiene acrylonitrile rubber, butyl rubbers, ethylene-propylene-diene terpolymers, isobutylene-isoprene copolymers, natural rubber adhesives, polychloroprenes, polyisobutylenes, polyisoprenes, polysiloxanes, styrene-butadiene-styrene block copolymers, styrene-isoprene-styrene block copolymers, vinyl ether polymers, and combinations thereof.

17. The composition of claim 16 wherein the hydrophobic polymer selected from the group consisting of butyl rubbers, polyisoprenes, styrene-butadiene-styrene block copolymers, styrene-isoprene-styrene block copolymers, and combinations thereof.

18. The composition of claim 1 wherein the hydrophobic polymer is selected from the group consisting of styrene-butadiene-styrene block copolymers and styrene-isoprene-styrene block copolymers, and further comprises a styrene-isoprene block copolymer.

19. The composition of claim 18 wherein the hydrophobic polymer mixture comprises up to 45 wt % of the styrene-isoprene block copolymer.

20. The composition of claim 1 wherein the elastomeric plasticizer is selected from the group consisting of low molecular weight polyisobutylenes, low molecular weight polyisoprene rubbers, styrene-based plasticizers, and combinations thereof.

21. The composition of claim 20 wherein the styrene-based plasticizers are selected from the group consisting of styrene-isoprene block copolymers, styrene-butadiene block copolymers, and combinations thereof.

22. The composition of claim 21 wherein the elastomeric plasticizer further comprises a low molecular weight polyisoprene rubber.

23. The composition of claim 1 wherein the tackifying resin is a non-polar tackifying resin selected from the group consisting of hydrogenated hydrocarbon resins, hydrocarbon resins and synthetic polyterpene resins.

24. The composition of claim 1 wherein the cellulose derived polymers are selected from the group consisting of hydroxypropylcellulose, hydroxypropylmethylcellulose and sodium carboxymethylcellulose.

25. The composition of claim 1 wherein the high molecular weight cellulose derived polymer has a molecular weight within the range of about 300–1,150 kg/mole.

26. The composition of claim 1 wherein the low molecular weight cellulose derived polymer has a molecular weight within the range of about 80–140 kg/mole.

27. The composition of claim 1 wherein the hydrophilic phase comprises at least one low molecular weight cellulose derived polymer and the weight ratio of low molecular weight cellulose derived polymers to high molecular weight cellulose derived polymers is about 1:1 to 1:2.

28. The composition of claim 1 wherein the hydrophilic phase comprises at least one naturally occurring polysaccharide and the weight ratio of naturally occurring polysaccharides to cellulose derived polymers is about 1:1 to 2:1.

29. The composition of claim 28 wherein the naturally occurring polysaccharide is selected from the group consisting of agars, alginates, carrageenans, chitin, chitosan, glucomannan, gum guar, gellan gum, locust bean gum, pectins, pullulan, starches and xanthans, and combinations thereof.

30. The composition of claim 29 wherein the naturally occurring polysaccharide is agar or starch.

31. The composition of claim 1 wherein the hydrophilic phase comprises a mixture of a low molecular weight cellulose derived polymer and a naturally occurring polysaccharide.

32. The composition of claim 1 wherein the reinforcing clay particles have an average diameter of about <15μ.

33. The composition of claim 1 wherein the clay particles are comprised of a phyllosilicate.

34. The composition of claim 33 wherein the phyllosilicate is montmorillonite.

35. The composition of claim 1 which further comprises an active agent.

36. The composition of claim 35 wherein the active agent is selected from the group consisting of antibiotics, antifungal agents, antiinflammatory agents, bacteriostatic and bactericidal compounds, caustic agents, keratolytic agents, pain relieving agents, proteolytic enzymes, tissue-healing enhancing agents, vasodilators, vessicants, and combinations thereof, and is present in a therapeutically effective amount.

37. The composition of claim 36 which further comprises a permeation enhancer.

38. The composition of claim 1 which further comprises at least one additive selected from the group consisting of adhesive agents, antioxidants, absorbent fillers, curing agents, preservatives, pH regulators, pigments, dyes, refractive particles, conductive species and antimicrobial agents.

39. The composition of claim 1 which is prepared by a blending and extruding process.

40. The composition of claim 39 wherein the hydrophilic phase comprises at least one low molecular weight cellulose derived polymer, and wherein: (1) the hydrophobic polymer, elastomeric plasticizer, tackifying resin, and clay particles are blended to form a mixture; (2) the mixture is heated to a temperature within the range of about 140–160° C.; and (3) the low and high molecular weight cellulose derived polymers are added to the mixture to form the composition.

41. The composition of claim 39 wherein the hydrophilic phase comprises at least one naturally occurring polysaccharide, and wherein (1) the tackifying resin and hydrophobic polymer are mixed to form a first mixture; (2) the polysaccharide, clay particles, and elastomeric plasticizer are mixed to form a second mixture; (3) the first mixture is heated to a temperature within the range of about 140–160° C.; (4) the high molecular weight cellulose derived polymer added to the first mixture; (5) the first mixture is cooled; and (6) the second mixture is added to the first mixture to form the composition.

42. A skin-contacting adhesive composition comprised of a hydrophobic phase and a hydrophilic phase, wherein:
(a) the hydrophobic phase comprises: a hydrophobic polymer selected from the group consisting of butadiene acrylonitrile rubber, butyl rubbers, ethylene-propylene-diene terpolymers, isobutylene-isoprene copolymers, natural rubber adhesives, polychioroprenes, polyisobutylenes, polyisoprenes, polysiloxanes, styrene-butadiene-styrene block copolymers, styrene-isoprene-styrene block copolymers, vinyl ether polymers, and combinations thereof; at least one elastomeric plasticizer and a tackifying resin; and
(b) the hydrophilic phase comprises:
  i) at least one material selected from the group consisting of low molecular weight cellulose derived polymers and naturally occurring polysaccharides;
  ii) at least one high molecular weight cellulose derived polymer; and
  iii) reinforcing clay particles.

43. The composition of claim 42 which comprises about 50–80 wt % hydrophobic phase and about 20–50 wt % hydrophilic phase.

44. The composition of claim 42 wherein the hydrophobic polymer is selected from the group consisting of butyl rubbers, polyisoprenes, styrene-butadiene-styrene block copolymers, styrene-isoprene-styrene block copolymers, and combinations thereof.

45. The composition of claim 42 wherein the hydrophobic polymer is selected from the group consisting of styrene-isoprene-styrene block copolymers and styrene-butadiene-styrene block copolymers, and further comprises a styrene-isoprene block copolymer.

46. The composition of claim 42 wherein the elastomeric plasticizer is selected from the group consisting of low molecular weight polyisobutylenes, low molecular weight polyisoprene rubbers, styrene-based plasticizers, and combinations thereof.

47. The composition of claim 42 wherein the tackifying resin is selected from the group consisting of hydrogenated hydrocarbon resins, hydrocarbon resins and synthetic polyterpene resins.

48. The composition of claim 42 wherein the high molecular weight cellulose derived polymer is selected from the group consisting of hydroxypropylcellulose, hydroxypropylmethylcellulose and sodium carboxymethylcellulose.

49. The composition of claim 42 wherein the hydrophilic phase comprises at least one low molecular weight cellulose derived polymer selected from the group consisting of hydroxypropylcellulose, hydroxypropylmethylcellulose and sodium carboxymethylcellulose.

50. The composition of claim 42 wherein the hydrophilic phase comprises at least one naturally occurring polysaceharide selected from the group consisting of agars, alginates, carrageenans, chitin, chitosan, glucomannan, gum guar, gellan gum, locust bean gum, pectins, pullulan, starches and xanthans, and combinations thereof.

51. The composition of claim 42 wherein the clay particles are comprised of montmorillonite.

52. The composition of claim 42 which further comprises a low molecular weight polyisobutylene.

53. The composition of claim 42 which further comprises an active agent selected from the group consisting of antibiotics, antifungal agents, antiinflammatory agents, bacteriostatic and bactericidal compounds, caustic agents, keratolytic agents, pain relieving agents, proteolytic enzymes, tissue-healing enhancing agents, vasodilators, vessicants, and combinations thereof, which is present in a therapeutically effective amount.

54. A skin-contacting adhesive composition comprised of a hydrophobic phase and a hydrophilic phase, wherein the hydrophilic phase comprises:
   i) randomly distributed spherical solid droplets comprised of a material selected from the group of low molecular weight cellulose derived polymers, naturally occurring polysaccharides, and combinations thereof;
   ii) fibers comprised of a liquid crystalline high molecular weight cellulose derived polymer; and
   iii) ordered particles comprised of clay.

* * * * *